(12) United States Patent
Narayan et al.

(10) Patent No.: US 8,815,828 B2
(45) Date of Patent: Aug. 26, 2014

(54) THERAPEUTIC COMBINATIONS FOR USE IN NEOPLASIA

(75) Inventors: Satya Narayan, Gainesville, FL (US); Aruna S. Jaiswal, Gainesville, FL (US); David A. Ostrov, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 293 days.

(21) Appl. No.: 12/997,199

(22) PCT Filed: Jun. 29, 2009

(86) PCT No.: PCT/US2009/003901
§ 371 (c)(1),
(2), (4) Date: Mar. 4, 2011

(87) PCT Pub. No.: WO2010/002454
PCT Pub. Date: Jan. 7, 2010

(65) Prior Publication Data
US 2011/0152206 A1    Jun. 23, 2011

Related U.S. Application Data

(60) Provisional application No. 61/133,949, filed on Jul. 2, 2008, provisional application No. 61/113,861, filed on Nov. 12, 2008.

(51) Int. Cl.
*A61K 31/70*    (2006.01)

(52) U.S. Cl.
USPC .......................................................... 514/48

(58) Field of Classification Search
USPC .......................................................... 514/48
See application file for complete search history.

(56) References Cited

U.S. PATENT DOCUMENTS

| | | | | |
|---|---|---|---|---|
| 6,004,948 | A * | 12/1999 | Blaschke et al. | 514/155 |
| 6,297,282 | B1 * | 10/2001 | Hartmann et al. | 514/603 |
| 7,378,421 | B2 * | 5/2008 | Mujica-Fernaud et al. | 514/254.11 |
| 8,304,416 | B2 * | 11/2012 | Mujica-Fernaud et al. | 514/254.11 |
| 2005/0227929 | A1 * | 10/2005 | Masferrer | 514/27 |
| 2008/0045529 | A1 * | 2/2008 | Eggenweiler et al. | 514/234.2 |

OTHER PUBLICATIONS

Suggitt et al. (Clin. Cancer Res. Feb. 1, 2005; 11: 971-981).*
Gura (Science. 1997; 278: 1041-1042).*
Dennis (Nature. Aug. 7, 2006; 442: 739-741).*
Cowled et al. (Cancer Res. Feb. 15, 1987; 47: 971-974).*
Saijo et al. (Cancer Sci. Oct. 2004; 95 (10): 772-776).*
Kelland (Eur. J. Cancer. Apr. 2004; 40 (6): 827-836).*
Bergers et al. (Current Opinion in Genetics and Development. 2000; 10: 120-127).*
Spiro et al. (Forum (Genova). Jul.-Sep. 2000; 10 (3): 274-85).*
Rabik et al. (Cancer Treat. Rev. Jun. 2006; 32 (4): 261-76).*
Connolly et al. (Br. J. Cancer. Jul. 15, 2002; 87 (2): 231-7).*
Jaiswal et al. (Mol. Cancer Res. Dec. 2009; 7 (12): 1973-83).*

* cited by examiner

*Primary Examiner* — Stephen Rawlings
(74) *Attorney, Agent, or Firm* — Edwards Wildman Palmer LLP; Peter F. Corless; Jeffrey D. Hsi

(57) ABSTRACT

The invention features compositions and methods that are useful for the treatment of neoplasia (e.g., breast cancer) by increasing DNA damage and reducing base excision repair (BER).

2 Claims, 9 Drawing Sheets

Figure 6

```
  1 mskrkapqet lnggitdmlt elanfeknvs qaihkynayr kaasviakyp
hkiksgaeak
 61 klpgvgtkia ekideflatg klrklekirq ddtsssinfl trvsgigpsa
arkfvdegik
121 tledlrkned klnhhqrigl kyfgdfekri preemlqmqd ivlnevkkvd
seyiatvcgs
181 frrgaessgd mdvllthpsf tsestkqpkl lhqvveqlqk vhfitdtlsk
getkfmgvcq
241 lpskndekey phrridirli pkdqyycgvl yftgsdifnk nmrahalekg
ftineytirp
301 lgvtgvagep lpvdsekdif dyiqwkyrep kdrse
```

Figure 9
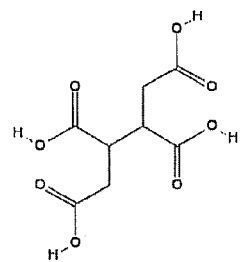
NSC21371
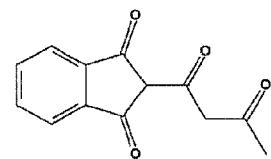
NSC91855
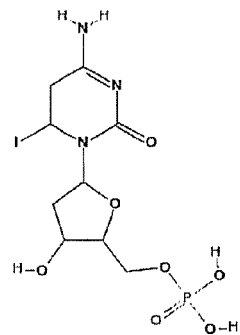
NSC124854
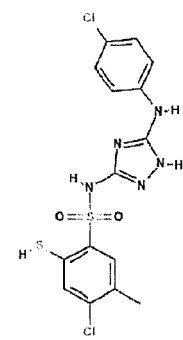
NSC666715

THERAPEUTIC COMBINATIONS FOR USE IN NEOPLASIA

CROSS-REFERENCE TO RELATED APPLICATION

This application is the U.S. National Phase Application, pursuant to 35 U.S.C. §371, of PCT International Application Serial No. PCT/US2009/003901, filed Jun. 29, 2009, and claims priority from U.S. Provisional Application No. 61/133,949, filed Jul. 2, 2008, and 61/113,861, filed Nov. 12, 2008, the entire contents of which are incorporated herein by reference.

STATEMENT OF RIGHTS TO INVENTIONS MADE UNDER FEDERALLY SPONSORED RESEARCH

This work was supported by the following grants from the National Institutes of Health, Grant No: RO1-CA100247. The government has certain rights in the invention.

BACKGROUND OF THE INVENTION

Breast cancer is one of the leading causes of morbidity and mortality in women worldwide. DNA repair pathways have been identified as a potential target for chemotherapeutic intervention of breast cancer growth. Normal cells actively repair DNA damage before going into mitosis and avoid DNA damage-induced killing of cells. In contrast, cancer cells possess defective mitotic signals and override the $G_0/G_1$ check point, but arrest in $G_2/M$ phase and face mitotic catastrophe and death.

Several DNA-alkylating drugs which induce DNA damage, such as Temozolomide (TMZ) and chloroethylnitrosoureas (CNU, BCNU, and ECNU), are listed in clinical trials. DNA damage induced by these alkylating drugs are primarily repaired by DNA polymerase β (Pol-β)-directed base excision repair (BER) pathway or the $O^6$-methylguanine DNA-methyltransferase (MGMT)/mismatch repair (MMR) pathway.

TMZ's utility as a breast cancer treatment is limited by life-threatening adverse events, such as thrombocytopenia (an abnormally low number of platelets, which help blood to clot), which occurs at the doses required to achieve efficacy, as well as unpleasant side effects, including fatigue, nausea, vomiting, anorexia, constipation, headache, and alopecia (hair loss). Methods for reducing TMZ dosage and enhancing chemotherapeutic efficacy are urgently required.

The development of new therapeutic approaches that exploit the expression of certain molecules (e.g., estrogen receptor, progesterone receptor, and human epidermal growth factor-2 receptor) has proven effective. At present, no effective treatment exists for breast cancers that do not express the estrogen receptor, progesterone receptor, and human epidermal growth factor-2 receptor. Such tumors are termed triple-negative (ER−/PR−/HER2−) breast cancers, and are associated with a high rate of local and systemic relapse.

SUMMARY OF THE INVENTION

The present invention features compositions and methods for enhancing the efficacy of DNA-alkylating drugs for the treatment of neoplasias (e.g., breast cancer).

In one aspect, the invention generally provides a method for treating breast cancer in a subject involving administering to the subject an effective amount of an alkylating agent, an agent that binds to $O^6$-methylguanine DNA-methyltransferase (MGMT) and reduces MGMT-mediated DNA repair relative to a reference, and an agent that binds to pol-β and an agent that binds to pol-β and reduces base extension repair relative to a reference, thereby treating the breast cancer.

In another aspect, the invention provides a method for treating breast cancer in a subject involving administering to the subject an effective amount of an alkylating agent, an agent that binds to $O^6$-methylguanine DNA-methyltransferase (MGMT) and reduces MGMT-mediated DNA repair relative to a reference, and an agent that binds pol-β at an adenomatous polyposis coli (APC) binding site.

In another aspect, the invention provides a method for treating breast cancer in a subject involving administering to the subject an effective amount of an alkylating agent, an agent that binds to pol-β and reduces base extension repair relative to a reference, and a chemopreventive agent, thereby treating the breast cancer.

In another aspect, the invention provides a method for treating breast cancer in a subject involving administering to the subject an effective amount of an alkylating agent, an agent that binds pol-β at an adenomatous polyposis coli (APC) binding site, and a chemopreventive agent.

In another aspect, the invention provides a method for treating breast cancer in a subject involving administering to the subject an effective amount of an alkylating agent, an agent that binds pol-β at an adenomatous polyposis coli (APC) binding site, a chemopreventive agent, and an agent that binds to $O^6$-methylguanine DNA-methyltransferase (MGMT) and reduces MGMT-mediated DNA repair relative to a reference.

In another aspect, the invention provides a method for treating a subject having breast cancer involving administering to the subject an effective amount of a pharmaceutical composition comprising an alkylating agent, $O^6$-benzylguanine, and NSC-666715 or NSC-124854.

In another aspect, the invention provides a method for treating breast cancer in a subject involving administering to the subject a combination containing an effective amount of a DNA alkylating agent; a pharmaceutical composition containing an agent that binds to $O^6$-methylguanine DNA-methyltransferase (MGMT) and reduces MGMT-mediated DNA repair, and a compound that is any one or more of NSC-666715, NSC-124854, NSC-21371 and NSC-91855, or an analog thereof, where the administration of the composition reduces the amount of the DNA alkylating agent required to treat the neoplasm, relative to the amount required to treat a neoplasm in a control subject.

In another aspect, the invention provides a method for treating a subject having breast cancer involving administering to the subject an effective amount of a pharmaceutical composition containing an alkylating agent, a chemopreventive agent, and NSC-666715 or NSC-124854.

In another aspect, the invention provides a method for treating breast cancer in a subject involving administering to the subject a combination containing an effective amount of a DNA alkylating agent; a pharmaceutical composition comprising a chemopreventive agent, and a compound that is any one or more of NSC-666715, NSC-124854, NSC-21371 and NSC-91855, or an analog thereof, where the administration of the composition reduces the amount of the DNA alkylating agent required to treat the neoplasm, relative to the amount required to treat a neoplasm in a control subject.

In another aspect, the invention provides a method of selecting an effective therapy for treating breast cancer in a subject involving identifying the subject as having breast cancer; and administering to the subject an alkylating agent, a chemopreventive agent, and an agent that binds to pol-β at an adenomatous polyposis coli (APC) binding site and reduces base extension repair.

In another aspect, the invention provides a pharmaceutical composition for the treatment of breast cancer, the composition containing an effective amount of a DNA alkylating agent, an agent that binds to $O^6$-methylguanine DNA-methyltransferase (MGMT) and reduces MGMT-mediated DNA repair, and an agent that binds to pol-β and reduces base extension repair.

In another aspect, the invention provides a pharmaceutical composition for the treatment of breast cancer, the composition comprising temozolomide, $O^6$-methyl guanine, and NSC-666715 or NSC-124854.

In another aspect, the invention provides a pharmaceutical composition for the treatment of breast cancer, the composition comprising an effective amount of a DNA alkylating agent, a chemopreventive agent, and an agent that binds to pol-β and reduces base extension repair.

In another aspect, the invention provides a pharmaceutical composition for the treatment of breast cancer, the composition comprising temozolomide, a chemopreventive agent, and NSC-666715 or NSC-124854. In one embodiment, the agent that binds to pol-β is a compound selected from the group consisting of NSC-124854, NSC-666715, NSC21371 and NSC91855, or an analog thereof. In another embodiment, the composition is labeled for the treatment of hormone/growth factor nonresponsive breast cancer. In yet another embodiment, the DNA alkylating agent is temozolomide. In still another embodiment, the agent that inhibits $O^6$-methylguanine DNA-methyltransferase is $O^6$-benzylguanine. In another embodiment, the chemopreventive agent is curcumin.

In another aspect, the invention provides a kit for the treatment of a neoplasia, the kit comprising an effective amount of an alkylating agent, an agent that reduces $O^6$-methylguanine DNA-methyltransferase activity, NSC-124854 or NSC-666715, and directions for the use of the kit for the treatment of a neoplasia.

In another aspect, the invention provides a kit for the treatment of a neoplasia, the kit comprising an effective amount of an alkylating agent, a chemopreventive agent, NSC-124854 or NSC-666715, and directions for the use of the kit for the treatment of a neoplasia. In one embodiment, the effective amount of the alkylating agent required to treat the neoplasia when administered in combination with an agent that inhibits $O^6$-methylguanine DNA-methyltransferase and NSC-124854 or NSC-666715 is less than the amount of alkylating agent administered alone. In another embodiment, the effective amount of the alkylating agent required to treat the neoplasia when administered in combination with the chemopreventive agent and NSC-124854 or NSC-666715 is less than the amount of alkylating agent administered alone.

In another aspect, the invention provides a method of selecting an effective therapy for treating breast cancer in a subject involving identifying the subject as having breast cancer; and administering to the subject an alkylating agent, an agent that binds to $O^6$-methylguanine DNA-methyltransferase (MGMT) and reduces MGMT-mediated DNA repair, and an agent that binds to pol-β at an adenomatous polyposis coli (APC) binding site and reduces base extension repair. Optionally, the method further involves administering a chemopreventive agent (e.g., curcumin).

In another aspect, the invention provides a method for increasing cytotoxicity of a chemotherapeutic agent in a subject involving administering to the subject NSC-124854 and/or NSC-666715, an alkylating agent and an agent that inhibits $O^6$-methylguanine DNA-methyltransferase.

In another aspect, the invention provides a method for increasing cytotoxicity of a chemotherapeutic agent in a subject involving administering to the subject NSC-124854 and/or NSC-666715, a chemopreventive agent, and an alkylating agent. In one embodiment, the alkylating agent is Temozolomide and the chemopreventive agent is curcumin. In another embodiment, the composition and the alkylating agent are administered within about 7, 8, 9, 10, 11, 12, 13, or 14 days, within about 1, 2, 3, 4, 5, or 6 days or are administered concurrently.

In another aspect, the invention provides a method for selecting a treatment for breast cancer in a subject involving identifying the subject as having a triple-negative ER⁻/PR⁻/HER2⁻ breast cancer, thereby identifying the subject as likely to benefit from treatment with NSC-124854 or NSC-666715, an alkylating agent and an agent that inhibits $O^6$-methylguanine DNA-methyltransferase and/or a chemopreventive agent. In one embodiment, the method further involves selecting a conventional neoplasia therapy that is any one or more of radical mastectomy, radiation therapy, hormone therapy, and chemotherapy.

In various embodiments of the above aspects, the agent that binds to pol-β is NSC-666715, NSC-124854, or an analog thereof. In other embodiments of the above-aspects, the APC binding site comprises amino acids Thr79, Lys81 and Arg83 of pol-β, and reduces pol-β-directed dRP-lyase activity or pol-β-directed strand-displacement synthesis. In other embodiments of the above-aspects, the alkylating agent is temozolomide, the agent that binds to $O^6$-methylguanine DNA-methyltransferase is $O^6$-benzylguanine, and the chemopreventive agent is curcumin. In other embodiments of the above-aspects, the breast cancer expresses one or more of an estrogen receptor, progesterone receptor, or human epidermal growth factor-2 receptor. In still other embodiments of the above-aspects, the breast cancer fails to express estrogen receptor, progesterone receptor, and human epidermal growth factor-2 receptor. In other embodiments of the above-aspects, the breast cancer is resistant to estrogen and/or progesterone, and/or is hormone nonresponsive. In other embodiments of the above-aspects, the agent that binds to pol-β reduces the activity of long patch- or single nucleotide-BER pathways relative to a reference. In other embodiments of the above-aspects, the agent that binds to pol-β reduces long patch- and single nucleotide-BER pathways. In other embodiments, an effective amount of a combination delineated herein has reduced toxicity relative to the administration of an effective amount of a DNA alkylating agent alone. In various embodiments of the above aspects, the DNA alkylating agent is temozolomide. In various embodiments of the above aspects, the inhibitor of $O^6$-methylguanine DNA-methyltransferase is $O^6$-benzylguanine. In various embodiments of the above aspects, the chemopreventive agent is curcumin. In still other embodiments, the method further comprises administering NSC-124854 and/or curcumin. In still other embodiments of the above aspects, the breast cancer is hormone responsive, hormone/growth factor responsive, or hormone/growth factor nonresponsive. In still other embodiments of the above aspects, the agent that binds to pol-β is NSC-666715, NSC-124854, or an analog thereof. In still other embodiments delineated herein, administration of an agent that binds to $O^6$-methylguanine DNA-methyltransferase (MGMT) and reduces MGMT-mediated DNA repair and NSC-666715 or NSC-124854 reduces the amount of an alkylating agent required to treat the breast cancer, relative to the amount required to treat an MMR-deficient breast cancer in a control subject. Preferably, this reduction is by at least about 5%, 10%, 20%, 30%, 40%, 50%, 60%, 75%, 85%, 95% or more. In other embodiments delineated herein, administration of curcumin reduces the amount of an alkylating agent required to treat the breast cancer, relative to the amount required to treat breast cancer in a control subject, such as a subject having a mismatch repair—deficient breast cancer. In other embodiments delineated herein, the breast cancer is resistant to conventional chemotherapy. In still other embodiments, the breast cancer is hormone responsive, hormone/growth factor responsive, or hormone/growth factor nonresponsive.

Other features and advantages of the invention will be apparent from the detailed description, and from the claims.

DEFINITIONS

By "alkylating agent" is meant a cytotoxic agent that transfers an alkyl group to a nucleophilic group on a molecule. Exemplary alkylating agents include, but are not limited to temozolomide, mechlorethamine, cyclophosphamide, chlorambucil, melphalan, ifosfamide, thiotepa, hexamethylmelamine, busulfan, altretamine, procarbazine, dacarbazine temozolomide, carmustine, lomustine, streptozocin, carboplatin, cisplatin, and oxaliplatin.

By "adenomatous polyposis coli (APC) binding site" is meant a portion of a pol-β polypeptide that interacts with an APC polypeptide.

By "binding to" a molecule is meant having a physicochemical affinity for that molecule.

By "chemopreventive agent" is meant any agent that reduces the risk of neoplasia in a subject having a propensity to develop a neoplasia.

By "computer modeling" is meant the application of a computational program to determine one or more of the following: the location and binding proximity of a ligand to a binding moiety, the occupied space of a bound ligand, the amount of complementary contact surface between a binding moiety and a ligand, the deformation energy of binding of a given ligand to a binding moiety, and some estimate of hydrogen bonding strength, van der Waals interaction, hydrophobic interaction, and/or electrostatic interaction energies between ligand and binding moiety. Computer modeling can also provide comparisons between the features of a model system and a candidate compound. For example, a computer modeling experiment can compare a pharmacophore model of the invention with a candidate compound to assess the fit of the candidate compound with the model.

By "conventional chemotherapeutic agent" is meant one or more chemical agents used in the treatment or control of proliferative diseases, including cancer. Chemotherapeutic agents include cytotoxic and cytostatic agents.

By "pol-β protein" is meant a polypeptide having at least about 85% identity to NCBI Accession No. P06746, or a fragment thereof having APC binding activity. An exemplary sequence for a human pol-β protein is provided at FIG. 6.

By "ameliorate" is meant decrease, suppress, attenuate, diminish, arrest, or stabilize the development or progression of a disease.

By "compound" is meant any small molecule chemical compound, antibody, nucleic acid molecule, or polypeptide, or fragments thereof.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "disease" is meant any condition or disorder that damages or interferes with the normal function of a cell, tissue, or organ.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "marker" is meant any protein or polynucleotide having an alteration in expression level or activity that is associated with a disease or disorder.

By "neoplasia" is meant a disease or disorder characterized by excess proliferation or reduced apoptosis. Illustrative neoplasms for which the invention can be used include, but are not limited to leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

By "protein" or "polypeptide" or "peptide" is meant any chain of more than two natural or unnatural amino acids, regardless of post-translational modification (e.g., glycosylation or phosphorylation), constituting all or part of a naturally-occurring or non-naturally occurring polypeptide or peptide, as is described herein.

By "subject" is meant a mammal, including, but not limited to, a human or non-human mammal, such as a bovine, equine, canine, ovine, or feline.

By "reference" is meant a standard or control condition. In one embodiment, the effect of an agent on a cell is compared to the effect of the agent on a control cell.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and most preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e.sup.-3 and e.sup.-100 indicating a closely related sequence.

"Therapeutic agent" means a substance that has the potential of affecting the function of an organism. Such a compound may be, for example, a naturally occurring, semisynthetic, or synthetic agent. For example, an agent may be a drug that targets a specific function of an organism or an antibiotic. A therapeutic agent may decrease, suppress, attenuate, diminish, arrest, or stabilize the development or progression of disease, disorder, or infection in a eukaryotic host organism.

BRIEF DESCRIPTION OF THE DRAWINGS

FIGS. 1A and 1B show the interaction of NSC-666715 and NSC-124854 molecules with Pol-β, respectively.

FIG. 2A shows a BER assay protocol. FIG. 2B shows an autoradiogram illustrating the effect of NSC-124854 and NSC-666715 on single nucleotide (SN) and long patch (LP) base excision repair activities. Data are representative of three different experiments.

FIG. 6 provides the amino acid sequence for a human DNA polymerase beta, which corresponds to NCBI Accession No. P06746 SEQ ID NO:2.

FIG. 9 provides structures of NSC124854; NSC666715; NSC21371; and NSC91855.

DETAILED DESCRIPTION OF THE INVENTION

Figure 1:
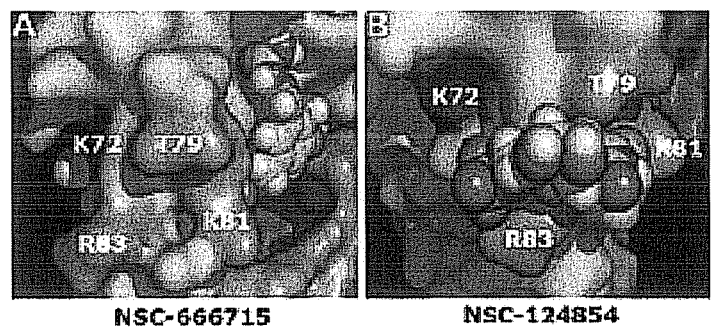
FIGS. 1A and 1B show the site selected for molecular docking (spheres in gold) is a cleft in the human Pol-β structure (blue and salmon) with appropriate chemical and geometric characteristics for binding small drug-like molecules.

The invention features compositions and methods that are useful for enhancing the efficacy of DNA-alkylating drugs for the treatment of neoplasia (e.g., breast cancer). In particular, the invention provides compositions comprising temozolomide (TMZ) in combination with one or all of NSC-666715 (Benzosulfonamide, 4-chloro-N-[5-[(4-chlorophenyl)amino]1H-1,2,4-triazol-3-yl]-2-mercapto-5-methyl-(9Cl)), NSC-124854 (5'-cytidylic acid, 2'-deoxy-6-iodo-(9Cl)), $O^6$-benzylguanine or curcumin; and methods of using the composition for the treatment of breast cancer. The invention is based, at least in part, on two surprising discoveries: first, that NSC-666715 and $O^6$-benzylguanine when administered in combination with temozolomide resulted in a 7-fold reduction in the $IC_{50}$ of TMZ; and second, that NSC-66715 and curcumin synergistically enhanced the effectiveness of TMZ by blocking base excision repair (BER), $O^6$-methylguanine DNA-methyltransferase (MGMT), and oncogenic signaling pathways in breast cancer cells with no or minimum effect on normal cells. Moreover, as reported herein, increases in temozolomide cytotoxicity were observed not only in hormone responsive (ER+/PR+) and hormone/growth factor responsive (ER+/PR+/HER2+) breast cancer cells, but the combination treatments were also surprisingly effective at inducing cell death in hormone/growth factor nonresponsive (ER-/PR-/HER2-) cells. In view of these discoveries, other agents, such as NSC-124854 (5'-cytidylic acid, 2'-deoxy-6-iodo-(9Cl)) that also bind APC within the active site are expected to be equally effective for the treatment of breast cancer, particularly hormone/growth factor nonresponsive breast cancers.

Breast Cancer

Breast cancer is one of the most frequently diagnosed cancer in women. Breast cancers are classified according to their expression of hormone/growth factor receptors into three groups: (i) Estrogen receptor (ER) and progesterone receptor (PR)-positive; (ii) Human epidermal growth factor receptor 2 (HER2)-positive; and (iii) ER, PR, and HER2-negative (triple-negative). For triple-negative breast tumors systemic chemotherapy is the only available therapeutic option. Although some therapeutic options are available for hormone/growth factor receptor-positive tumors, these therapies have a number of drawbacks that limit their utility. Hormone receptor-positive tumors are managed with ER-targeted therapy options in combination with chemotherapy (Arnedos et al., Expert Rev. Anticancer Ther. 7: 1651-1664, 2007; Ellis, J. Natl. Cancer Inst. 100: 159-161, 2008).

The anti-estrogen, tamoxifen, has been used for more than two decades to treat hormone-dependent breast cancers and provides great benefit to patients when used as a systemic adjuvant therapy after surgery for early breast cancer and for specific follow-up periods. However, prolonged tamoxifen therapy has no additional usefulness at four years follow-up, and some women treated with tamoxifen develop endometrial cancer, gynecologic symptoms, and thromboembolic events. The risk of such adverse developments can be reduced by treatment with SERM raloxifene, ICI-164,384, ICI-182,780, and aromatse inhibitors. The HER2-positive tumors are managed with HER2-directed therapy with Trastuzumab or Lapatinib and very recently Bevacizumab or Avastin (Genentech) has received accelerated approval from the US Food and Drug Administration (FDA) for use in HER2-positive metastatic breast tumors in combination with paclitaxel chemotherapy. Although Avastin in combination with paclitaxel seems to be clearly useful for the management of HER2-positive tumors, its use requires great caution due to its side-effects.

Increased knowledge of the tumorigenesis cascade in breast cancer has led to directed therapeutic approaches that are tailored to specific tumor type, i.e., either ER-positive, PR-positive tumors or HER2-positive tumors, or triple-negative tumors. In addition to this heterogeneity, the microarray gene profiling data that has been generated in the past several years suggest an even greater heterogeneity of tumor type. As the available treatment modalities depend largely on the hormone/growth factor receptor status of the tumor, such an approach requires the development of an alternative chemotherapeutic/chemopreventive strategy. The present invention provides a treatment strategy that can be used to manage all of these types of tumors, and therefore represents a major advance in patient care. The present invention is founded on the recognition that combinatorial therapeutic strategies can provide dramatic improvements over mono-therapeutic regimens.

In particular embodiments, the invention provides compositions and methods for the treatment of neoplasia featuring temozolomide in combination with any one or more of NSC-124854, NSC-666715, and curcumin (NSC-32982), a chemopreventive agent from the plant *Curcuma longa*. The non-toxic natural chemopreventive agents have been shown to enhance the anti-tumor activity of chemotherapeutic agents. A combination of chemopreventive and chemotherapeutic agents to block DNA repair and multiple oncogenic pathways is more efficacious than the use of single agents for the management of ER/PR/HER2-responsive and triple-negative breast cancers.

In other embodiments, the invention features compositions and methods that are useful for the treatment of a neoplasia (e.g., breast cancer) by potentiating the efficacy of DNA alkylating agents using small molecules that interfere with the Base Excision Repair (BER) and $O^6$-methylguanine DNA-methyltransferase (MGMT)/mismatch repair (MMR) DNA repair pathways. The chemotherapeutic drugs, which induce DNA-alkylation damage, are primarily repaired by the MGMT, MMR, and BER pathways. Anticancer drugs as inhibitors of these DNA-repair systems have emerged, but the targets have been mainly the MGMT and MMR pathways. The blockade of the BER pathway has been largely overlooked, although in the case of DNA-alkylating drug, Temozolomide (TMZ), BER is responsible for the repair of 70% and 9% of $N^7$-Methyl guanine and $N^3$-methyl adenine lesions, respectively. Structure-based screening of small molecular weight inhibitors identified small molecule inhibitors (SMIs), including NSC-124854 and NSC-666715 that interact with APC within the active site of Pol-β and block the Pol-β-directed BER pathway. Accordingly, use of these inhibitors in combination with TMZ, or other alkylating agents, synergistically increases therapeutic efficacy, reduces adverse side effects, thereby providing an advance over existing monotherapies.

The Base Excision Repair (BER) Pathway

Exogenous and endogenous mutagenic agents attack the genomes of all living cells. DNA bases damaged by these agents may be cytotoxic and/or miscoding, and are thought to be a major source of intermediates in tumorigenesis. DNA repair systems efficiently remove damaged DNA via several different pathways that reverse the vast majority of genetic lesions formed during the life span of a cell. Most DNA repair mechanisms, including the base excision repair pathway, involve the participation of enzymes and other proteins that recognize structural alterations in DNA. Estimates of the number of abasic sites generated by mammalian cells are approximately $10^6$/cell/day. Abasic sites are unstable and degrade spontaneously into DNA-strand breaks by β-elimination that retards DNA polymerases. They are highly mutagenic because of non-template DNA and RNA synthesis. Despite the large number of abasic sites generated per cell per day, the number of resulting mutations is extremely low.

This disparity underscores the importance of the elaborate mechanisms that the cell has devised to repair abasic sites. Deficiencies in the DNA repair pathways usually have catastrophic consequences for the affected organisms. In humans, deficiency in DNA repair has been linked to a number of genetic diseases characterized by radiation sensitivity and cancer-prone syndromes.

For instance, there is evidence that predisposition of certain colon tumors result from defects in DNA mismatch repair (MMR) system. About 15% of hereditary nonpolyposis colon cancers (HNPCC) have defects in one or more proteins in the MMR pathway. Also, mutations and/or different levels of expression of DNA polymerase β, pol-β gene have been observed in many colon and lung tumors and cancer cell lines, indicating that a base excision repair defective pathway is associated with cancer development.

In mammalian cells, base excision repair can proceed through at least two pathways distinguished by the repair patch size as well as by the contribution of different proteins involved in the pathway. These are designated as "single nucleotide (SN)-base excision repair" and "multinucleotide or long-patch (LP)-base excision repair" pathways. In both pathways, repair is initiated by the initial recognition and removal of the modified base by a DNA glycosylase generating an abasic site (AP-site). There are two types of DNA glycosylases—monofunctional and bifunctional. Monofunctional DNA glycosylases cleave only the glycosidic bond between N and C1' and then protect the abasic site until apurinic/apyrimidinic (AP) endonuclease 1 (APE-1) cleaves the DNA backbone at the 5'-end of the AP-site. The bifunctional DNA glycosylases have additional AP-lyase activity. The DNA glycosylase cleaves a glycosidic bond between the sugar and the base to establish an abasic-site. Subsequently, APE-1 cleaves the DNA backbone generating a 3'-OH and 5'-deoxyribose phosphate (5'-dRP) ends. Subsequently, the remaining 5'-dRP residue is cleaved by a 5'-deoxyribose phosphate lyase (dRP-lyase) activity of pol-β to yield a 5'-phosphorylated gapped-DNA strand. Pol-β then incorporates the correct base at the site of the damaged base with its polymerizing activity and DNA ligase-I or III seals the nick. This repair process becomes complicated once the AP-site is oxidized or reduced. In this case, the dRP-lyase activity of pol-β is interrupted and the repair of DNA is accomplished through long patch-base excision repair. Under these circumstances, the pol-β-dependent strand-displacement synthesis generates longer repair patch and a 5'-overhang of a single-stranded DNA-flap with a modified sugar at its 5'-end. The 5'-overhang DNA-flap is cleaved by flap endonuclease 1 (Fen-1), and finally the nick is sealed by DNA ligase I or III.

The DNA polymerase β (Pol-β)-directed base excision repair (BER) pathway or the $O^6$-methylguanine DNA-methyltransferase (MGMT)/mismatch repair (MMR) pathways play a key role in the responses of cells to alkylating agents that damage DNA. Indeed, the extent and type of DNA damage incurred on exposure to the alkylating agents plays a role in determining the type of BER response. It also determines whether the cell continues to attempt to repair the damage, or in the face of extensive damage, switches to an apoptotic response to eliminate the cell. The latter phenomenon is exploited in the use of alkylating agents as chemotherapeutic agents. It is well established that APC, which is generally considered to act as a tumor suppressor, plays a key role at least in colorectal carcinogenesis, and interacts with DNA polymerase β (Pol-β) in the base excision repair (BER) pathway.

As reported in more detail below, the treatment of human breast cancer cells with the DNA alkylating agent temozolomide (TMZ) increases DNA damage, which requires the activity of the BER and MGMT/MMR pathways for DNA repair. Blocking either the BER pathway, the MGMT/MMR pathways, or both result in increased sensitivity and cell death of cells harboring damaged DNA. In addition, exposure of human breast cancer cell lines to a Pol-β inhibitor, e.g., NSC-666715, enhanced the cytotoxicity of TMZ. Furthermore exposure of human breast cancer cell lines to a combination of a Pol-β inhibitor, e.g., NSC-666715 and BG further enhanced the cytotoxicity of TMZ.

Pol-β

Pol-β is the smallest eukaryotic DNA polymerase. It is a 39-kDa protein and consists of an 8-kDa amino-terminal domain with dRP-lyase and 5'-phosphate recognition activities, and a 31-kDa carboxyl-terminal domain with nucleotidyltransferase activity (Beard et al., (2006) Chem. Rev. 106, 361-382). The 8- and 31-kDa domains of pol-β are connected by a protease-hypersensitive region, known as the linker-region (Kumar et al., (1990) Biochemistry 29, 7156-7159; Beard, W. A., and Wilson, S. H. (1995) Methods Enzymol. 262, 98-107). Pol-β has the ability to fill short DNA gaps, but lacks an associated exonuclease or proofreading activity (Singhal, R. K., and Wilson, S. H. (1993) J. Biol. Chem. 268, 15906-15911). The 31-kDa carboxyl-terminal polymerase domain is composed of three functionally distinguishable subdomains. First, the catalytic C-subdomain, which coordinates two divalent metal cations, assists the nucleotidyl transferase reaction in base excision repair. Second, the D-subdomain which has a primary role in duplex DNA-binding; and the N-subdomain provides interactions with the nascent base pair (nucleoside 5'-triphosphate and templating nucleotide) (Beard et al., (2006) Chem. Rev. 106, 361-382). These subdomains correspond to the palm, thumb, and fingers subdomains, respectively, for right-handed DNA polymerases (Beard et al., (2006) Chem. Rev. 106, 361-382, 35).

The crystal and solution structures of the amino-terminal 8-kDa lyase domain (amino acids 1-87) have been determined (Pelletier et al., (1994) Science 264, 1891-1903, Liu et al., (1996) Biochemistry 35, 6188-6200). This domain is composed of two pairs of antiparallel α-helices and possesses the dRP-lyase activity. The lyase domain also contains a motif termed "Helix-hairpin-Helix (HhH)", which is common in many other DNA repair proteins (Pelletier, H., and Sawaya, M. R. (1996) Biochemistry 35, 12778-12787). Biochemical and crystallography studies indicate that Lys72 plays a role in the lyase reaction mechanism. This reaction proceeds via a Schiff-base intermediate between pol-β and the 5'-dRP residue of the substrate, whereby the side chain of Lys72 provides the nucleophile for the completion of the reaction. The involvement of the lyase domain in strand-displacement synthesis of pol-β remains to be identified.

Adenomatous Polyposis Coli

Mutation of the adenomatous polyposis coli (APC), a tumor suppressor gene is an early event in familial adenomatous polyposis (FAP), a syndrome in which there is an inherited predisposition to colon cancer. The amino acid sequence of APC is provided at NCBI Reference No. NP_000029, which is reproduced below as SEQ ID NO:1:

```
  1 maaasydqll kqvealkmen snlrqeledn snhltklete asnmkevlkq lqgsiedeam 61 assgqidlle rlkelnldss nfpgvklrsk mslrsygsre gsyssrsgec spvpmgsfpr 121 rgfvngsres tgyleeleke rsllladldk eekekdwyya qlqnltkrid slpltenfsl
```

```
 181 qtdmtrrqle yearqirvam eeqlgtcqdm ekraqrriar iqqiekdilr irqllqsqat
 241 eaerssqnkh etgshdaerq negqgvgein matsgngqgs ttrmdhetas vlsssssthsa
 301 prrltshlgt kvemvyslls mlgthdkddm srtllamsss qdscismrqs gclplliqll
 361 hgndkdsvll gnsrgskear arasaalhni ihsqpddkrg rreirvlhll eqiraycetc
 421 wewqeahepg mdqdknpmpa pvehqicpav cvlmklsfde ehrhamnelg glqaiaellq
 481 vdcemygltn dhysitlrry agmaltnltf gdvankatlc smkgcmralv aqlksesedl
 541 qqviasvlrn lswradvnsk ktlrevgsvk almecalevk kestlksvls alwnlsahct
 601 enkadicavd galaflvgtl tyrsqtntla iiesgggilr nvssliatne dhrqilrenn
 661 clqtllqhlk shsltivsna cgtlwnlsar npkdqealwd mgavsmlknl ihskhkmiam
 721 gsaaalrnlm anrpakykda nimspgsslp slhvrkqkal eaeldaqhls etfdnidnls
 781 pkashrskqr hkqslygdyv fdtnrhddnr sdnfntgnmt vlspylnttv lpsssssrgs
 841 ldssrsekdr slerergigl gnyhpatenp gtsskrglqi sttaaqiakv meevsaihts
 901 qedrssgstt elhcvtdern alrrssaaht hsntynftks ensnrtcsmp yakleykrss
 961 ndslnsvsss dgygkrgqmk psiesysedd eskfcsygqy padlahkihs anhmddndge
1021 ldtpinyslk ysdeqlnsgr qspsqnerwa rpkhiiedei kqseqrqsrn qsttypvyte
1081 stddkhlkfq phfgqqecvs pyrsrgangs etnrvgsnhg inqnvsqslc qeddyeddkp
1141 tnyserysee eqheeeerpt nysikyneek rhvdqpidys lkyatdipss qkqsfsfsks
1201 ssgqsskteh mssssentst pssnakrqnq lhpssaqsrs gqpqkaatck vssinqetiq
1261 tycvedtpic fsrcsslssl ssaedeigcn qttqeadsan tlqiaeikek igtrsaedpv
1321 sevpavsqhp rtkssrlqgs slssesarhk avefssgaks psksgaqtpk sppehyvqet
1381 plmfsrctsv ssldsfesrs iassvqsepc sgmvsgiisp sdlpdspgqt mppsrsktpp
1441 pppqtaqtkr evpknkapta ekresgpkqa avnaavqrvq vlpdadtllh fatestpdgf
1501 scssslsals ldepfiqkdv elrimppvqe ndngnetese qpkesnenqe keaektidse
1561 kdllddsddd dieileecii samptkssrk akkpaqtask lpppvarkps qlpvykllps
1621 qnrlqpqkhv sftpgddmpr vycvegtpin fstatslsdl tiesppnela agegvrggaq
1681 sgefekrdti ptegrstdea qggktssvti pelddnkaee gdilaecins ampkgkshkp
1741 frvkkimdqv qqasasssap nknqldgkkk kptspvkpip qnteyrtrvr knadsknnln
1801 aervfsdnkd skkqnlknns kvfndklpnn edrvrgsfaf dsphhytpie gtpycfsrnd
1861 slssldfddd dvdlsrekae lrkakenkes eakvtshtel tsnqqsankt qaiakqpinr
1921 gqpkpilqkq stfpqsskdi pdrgaatdek lqnfaientp vcfshnssls slsdidqenn
1981 nkenepiket eppdsqgeps kpqasgyapk sfhvedtpvc fsrnsslssl sidseddllq
2041 ecissampkk kkpsrlkgdn ekhsprnmgg ilgedltldl kdiqrpdseh glspdsenfd
2101 wkaiqegans ivsslhqaaa aaclsrqass dsdsilslks gislgspfhl tpdqeekpft
2161 snkgprilkp gekstletkk ieseskgikg gkkvykslit gkvrsnseis gqmkqplqan
2221 mpsisrgrtm ihipgvrnss sstspvskkg pplktpasks psegqtatts prgakpsvks
2281 elspvarqts qiggsskaps rsgsrdstps rpaqqplsrp iqspgrnsis pgrngisppn
2341 klsqlprtss pstastkssg sgkmsytspg rqmsqqnltk qtglsknass iprsesaskg
2401 lnqmnngnga nkkvelsrms stkssgsesd rserpvlvrq stfikeapsp tlrrkleesa
2461 sfeslspssr pasptrsqaq tpvlspslpd mslsthssvq aggwrklppn lsptieyndg
2521 rpakrhdiar shsespsrlp inrsgtwkre hskhssslpr vstwrrtgss ssilsasses
2581 sekaksedek hvnsisgtkq skenqvsakg twrkikenef sptnstsqtv ssgatngaes
```

```
2641 ktliyqmapa vsktedvwvr iedcpinnpr sgrsptgntp pvidsveska npnikdskdn 2701 qakqnvgngs vpmrtvglen rlnsfiqvda pdqkgteikp gqnnpvpvse tnessivert 2761 pfssssskh  sspsgtvaar vtpfnynpsp rkssadstsa rpsqiptpvn nntkkrdskt 2821 dstessgtqs pkrhsgsylv tsv
```

APC is expressed constitutively within the normal colonic epithelium. Little is known about how mutations of (or abnormal expression of) APC contribute to the development of colon cancer. The APC gene product is a 310-kDa-homodimeric protein localized in both the cytoplasm and the nucleus. APC is known to play a diversified role in cell migration, cell-cell adhesion, β-catenin regulation, cellular proliferation and chromosomal segregation. Notably, mutations in the APC gene also are found in 60 to 80% of sporadic colorectal cancers and adenomas. Thus, it is now established that mutations in APC may be necessary for the early onset of polyposis. Whether APC mutations may contribute to the accumulation of mutations in other genes that are associated with colon cancer progression remains unclear. Mutations in the APC gene are associated with an early onset of colorectal carcinogenesis.

The interaction of APC with pol-β has been mapped, and residues Thr79, Lys81 and Arg83 of the linker-region of pol-β protein were discovered to function in the interaction with APC. Interaction of APC with pol-β blocks both strand-displacement DNA synthesis and single nucleotide-base excision repair by inhibiting the deoxyribose phosphate-lyase activity of pol-β. Mutational analysis of pol-β identified the role of APC in the base excision repair function of pol-β. The pol-β Mut-1 protein (T79A/K81A/R83A) blocked strand-displacement DNA synthesis and long patch-base excision repair with both uracil and tetrahydrofuran DNA substrates. Abasic sites in DNA are induced by stressors such as spontaneous oxidation/reduction, alkylation and temperature changes and are repaired primarily by single-nucleotide (SN)- or long-patch (LP)-base excision repair pathways. APC also interacts with flap endonuclease 1 (Fen-1) and mediates inhibition of long patch-base excision repair is due to blockage of Fen-1 activity. The interaction of APC with pol-β describe a role for APC in regulating both long patch- and single nucleotide-base excision repair pathways and suggest a function of the linker-region of pol-β in base excision repair activity. Moreover, these results suggest a role for APC in base excision repair and chemoprevention.

Curcumin: A Chemopreventive Agent

Curcumin [(1E,6E)-1,7-bis(4-hydroxy-3-methoxy-phenyl)hepta-1,6-diene-3,5-dione; NSC-32982, commonly known as diferuloylmethane] is a hydrophobic polyphenol known for its powerful anti-cancer, anti-oxidant, anti-amyloid and anti-inflammatory properties (Anand et al., Cancer Lett. 267: 133-164, 2008). The anti-cancer effects of curcumin stem from its ability to induce apoptosis in cancer cells without cytotoxic effects on healthy cells. Several studies have described the anticancer activity of curcumin in a variety of breast cancer cell lines, including hormone-dependent, hormone-independent, and multi-drug-resistant cells (Aggarwal et al., Turmeric Genus *Curcuma*, CRC Press, NY, pp. 297-368, 2007). In a human breast cancer xenograft model study, treatment with curcumin resulted in a decreased incidence of breast cancer growth and metastasis in nude mice (Aggarwal et al., Clin. Cancer Res. 11: 7490-7498, 2005). There is accumulating evidence in the literature suggesting that curcumin has a diverse range of molecular targets, supporting the concept that it acts upon numerous biochemical and molecular cascades. Some of the well-known molecular targets for curcumin are the activation of transcription factors such as transcription factors activator protein 1 (AP-1), nuclear factor-kappa B (NF-κB), signal transducers and activators of transcription 3 (STAT-3), early growth response gene 1 (EGR-1), hypoxia inducible factor 1 (HIF-1), peroxisome proliferator-activated receptor (PPAR-γ), Bcl-xL, and Notch-1. Curcumin inhibits colon cancer growth by inhibiting β-catenin-mediated c-myc gene expression and disrupting cell-cell adhesion (Jaiswal et al., Oncogene 21: 8414-8427, 2002). It is also reported that curcumin suppresses ERalpha-responsive breast cancer cell growth both in vitro and in vivo (Somers-Edgar et al., Int. J. Cancer 122: 1966-1971, 2008). Activation of these transcription factors are involved in cell proliferation, cell invasion, metastasis, angiogenesis, and resistance to chemotherapy and radiotherapy.

As reported herein, NSC-124854, NSC-666715, and curcumin NSC-32982 block TMZ-induced repair of DNA lesions through a mechanism associated with a block in the BER pathway. Furthermore, these results indicate that curcumin likely acts to inhibit tumor growth by inhibiting multiple signaling pathways. However, the mechanisms by which a combination of these agents produces a synergistic effect with TMZ in the elimination of breast cancer cells is not known and the possibility that there is an interaction between DNA repair and oncogenic pathways has not been explored in depth. The present analysis of the molecular and cellular mechanism by which SMI and curcumin-induced efficacy of TMZ in breast tumors in an orthotopic xenograph-model provides for the management of patients with ER/PR/HER2-responsive or non-responsive (triple-negative) breast tumors, and most importantly for patients diagnosed with metastasis.

Base Excision Repair as a Chemotherapeutic Target

Defects in the base excision repair pathway can cause cytotoxic accumulation of lesions in cell genomic DNA. This accumulation of lesions has been exploited as a chemotherapeutic target for killing cancer cells. DNA-alkylating agents are commonly used to induce genetic lesions in cancer cells for the treatment of brain tumors, ovarian cancer, malignant melanomas, and various hematological tumors. These DNA-alkylating agents have either one or two reactive groups that interact covalently with nucleophilic centers in DNA. Such reactive sites are present in all four bases, and they are attacked with different affinities and specificities. Most reactive sites are the ring nitrogen atoms—in particular $N^7$ of guanine ($N^7mG$) and $N^3$ of adenine ($N^3mA$), but alkylation also occurs at less nucleophilic oxygens, such as the $O^6$ position of guanine ($O^6mG$). The $N^7mG$ and $N^3mA$ are very common lesions and under normal circumstances they are repaired by base excision repair. Although a number of pol-β inhibitors have been reported, more potent and selective inhibitors of DNA pol-β are still needed. One approach to the identification of such agents is to sensitize cancer cells to DNA-damaging agents by inhibiting various proteins in the DNA repair pathways. Small chemical compounds have been identified by molecular docking or NMR studies to target the base excision repair pathway by inhibiting apurinic/apyrimidinic endonuclease and pol-β activities. For pol-β, the most active compound identified by NMR chemical shift mapping is pamoic acid. This compound inhibits dRP-lyase activity, blocks only single nucleotide-base excision repair of pol-β, which occurs at a high concentration. Since abasic DNA damage can also be repaired by long patch-BER, there is a need for agents that can block both pol-β directed single nucleotide- and long patch-base excision repair pathways. APC interacts with pol-β and blocks both SN- and LP-BER pathways. Thus, APC and APC mimetics may be used to target pol-β-mediated sensitization of cancer cells.

Compounds of the Invention

Compounds, such as NSC-666715 and NSC-124854, and other compounds that bind to amino acid residues of Pol-β that function in mediating the interaction of Pol-β with APC (e.g., Thr79, Lys81 and Arg83) are useful for the treatment of neoplasias, such as breast cancer, glioblastomas, lung cancer, and colon cancer, alone or in combination with an alkylating agent, such as temozolomide. Without wishing to be bound by theory, these compounds may be particularly effective against neoplastic cells because they are capable of interacting with and reducing the activity of pol-β. In one approach, compounds useful for the treatment of neoplasia are selected using a molecular docking program to identify compounds that bind to pol-β at an APC binding site (e.g., a pol-β site comprising at least amino acid residues Thr79, Lys81 and Arg83). In certain embodiments, a compound of the invention binds to pol-β and reduces BER activity, pol-β-directed dRP-lyase activity, or pol-β-directed strand-displacement synthesis.

In certain embodiments, a compound of the invention can prevent, inhibit, or disrupt, or reduce by at least 10%, 25%, 50%, 75%, or 100% the activity of a BER pathway by binding to an APC binding site in pol-β.

In certain embodiments, a compound of the invention is a small molecule having a molecular weight less than about 1000 daltons, less than 800, less than 600, less than 500, less than 400, or less than about 300 daltons. Examples of compounds of the invention include NSC-124854 and NSC-666715, and pharmaceutically acceptable salts thereof.

The term "pharmaceutically acceptable salt" also refers to a salt prepared from a compound of the invention having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)-amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)-amine, or tri-(2-hydroxyethyl)amine; N-methyl-D-glucamine; and amino acids such as arginine, lysine, and the like. The term "pharmaceutically acceptable salt" also refers to a salt prepared from a compound disclosed herein, e.g., NSC-124854 and NSC-666715 having a basic functional group, such as an amino functional group, and a pharmaceutically acceptable inorganic or organic acid. Suitable acids include, but are not limited to, hydrogen sulfate, citric acid, acetic acid, oxalic acid, hydrochloric acid, hydrogen bromide, hydrogen iodide, nitric acid, phosphoric acid, isonicotinic acid, lactic acid, salicylic acid, tartaric acid, ascorbic acid, succinic acid, maleic acid, besylic acid, fumaric acid, gluconic acid, glucaronic acid, saccharic acid, formic acid, benzoic acid, glutamic acid, methanesulfonic acid, ethanesulfonic acid, benzenesulfonic acid, and p-toluenesulfonic acid.

An anti-neoplasia therapeutic, such as NSC-124584 and NSC-666715, may be administered in combination with any other standard anti-neoplasia therapy or conventional chemotherapeutic agent, such as an alkylating agent; such methods are known to the skilled artisan and described in Remington's Pharmaceutical Sciences by E. W. Martin. If desired, agents of the invention are administered in combination with any conventional anti-neoplastic therapy, including but not limited to, surgery, radiation therapy, or chemotherapy. Conventional chemotherapeutic agents include, but are not limited to, alemtuzumab, altretamine, aminoglutethimide, amsacrine, anastrozole, azacitidine, bleomycin, bicalutamide, busulfan, capecitabine, carboplatin, carmustine, celecoxib, chlorambucil, 2-chlorodeoxyadenosine, cisplatin, colchicine, cyclophosphamide, cytarabine, cytoxan, dacarbazine, dactinomycin, daunorubicin, docetaxel, doxorubicin, epirubicin, estramustine phosphate, etodolac, etoposide, exemestane, floxuridine, fludarabine, 5-fluorouracil, flutamide, formestane, gemcitabine, gentuzumab, goserelin, hexamethylmelamine, hydroxyurea, hypericin, ifosfamide, imatinib, interferon, irinotecan, letrozole, leuporelin, lomustine, mechlorethamine, melphalen, mercaptopurine, 6-mercaptopurine, methotrexate, mitomycin, mitotane, mitoxantrone, nilutamide, nocodazole, paclitaxel, pentostatin, procarbazine, raltitrexed, rituximab, rofecoxib, streptozocin, tamoxifen, temozolomide, teniposide, 6-thioguanine, topotecan, toremofine, trastuzumab, vinblastine, vincristine, vindesine, and vinorelbine. In one preferred embodiment, an agent that binds to an APC binding site on pol-β (e.g., APC or an APC mimetic, such as NSC-124584 and NSC-666715) and reduces pol-β activity is administered in combination with temozolomide. In another preferred embodiment, an agent that binds to an APC binding site on pol-β (e.g., APC or an APC mimetic, such as NSC-124584 and NSC-666715) and reduces pol-β activity and an agent that binds to $O^6$-methylguanine DNA-methyltransferase (MGMT) and reduces MGMT-mediated DNA repair or a chemopreventive agent (e.g., curcumin) are administered in combination with temozolomide.

In Silico Screening Methods and Systems

Methods for designing, evaluating and identifying compounds that bind to the aforementioned binding site are apparent to one of skill in the art using a machine readable storage medium which comprises the structural coordinates of an APC binding site in pol-β identified herein (e.g., aminio acids 60-120, 60-170, 80-170, or another fragment containing Thr79, Lys81 and Arg83). A storage medium encoded with these data is capable of displaying a three-dimensional graphical representation of a molecule or molecular complex which comprises such binding sites on a computer screen or similar viewing device. Compounds identified in such a way are expected to be cytotoxic, to inhibit pol-β biological activity (e.g., pol-β-directed dRP-lyase activity, pol-β-directed strand-displacement synthesis) and/or to reduce the activity of a BER pathway. A computer may be used for producing a) a three-dimensional representation of a molecule or molecular complex, wherein said molecule or molecular complex comprises a binding site; or b) a three-dimensional representation of a homologue of said molecule or molecular complex, wherein said homologue comprises a binding site that has a root mean square deviation from the backbone atoms of said amino acids of not more than about 2.0 (more preferably not more than 1.5) angstroms. Such a computer may comprise:

(i) a machine-readable data storage medium comprising a data storage material encoded with machine-readable data, wherein said data comprises the structure coordinates of amino acid residues in the pol-β APC binding site;

(ii) a working memory for storing instructions for processing said machine-readable data;

(iii) a central-processing unit coupled to said working memory and to said machine-readable data storage medium for processing said machine readable data into said three-dimensional representation; and (iv) a display coupled to said central-processing unit for displaying said three-dimensional representation.

Thus, the computer produces a three-dimensional graphical structure of a molecule or a molecular complex which comprises a binding site.

The computer may also comprise a machine-readable data storage medium for producing a three-dimensional representation of a molecule or molecular complex defined by structure coordinates of all of the pol-β amino acids, or a three-dimensional representation of a homologue of said molecule or molecular complex, wherein said homologue comprises a binding site that has a root mean square deviation from the backbone atoms of said amino acids of not more than 2.0 (more preferably not more than 1.5) angstroms.

In exemplary embodiments, the computer or computer system can include components that are conventional in the art, e.g., as disclosed in U.S. Pat. Nos. 5,978,740 and/or 6,183,121 (incorporated herein by reference). For example, a computer system can include a computer comprising a central processing unit ("CPU"), a working memory (which may be, e.g., RAM (random-access memory) or "core" memory), a mass storage memory (such as one or more disk drives or CD-ROM drives), one or more cathode-ray tube (CRT) or liquid crystal display (LCD) display terminals, one or more keyboards, one or more input lines, and one or more output lines, all of which are interconnected by a conventional system bus.

Machine-readable data of this invention may be inputted to the computer via the use of a modem or modems connected by a data line. Alternatively or additionally, the input hardware may include CD-ROM drives, disk drives or flash memory. In conjunction with a display terminal, a keyboard may also be used as an input device.

Output hardware coupled to the computer by output lines may similarly be implemented by conventional devices. By way of example, output hardware may include a CRT or LCD display terminal for displaying a graphical representation of a binding pocket of this invention using a program such as QUANTA or PYMOL. Output hardware might also include a printer, or a disk drive to store system output for later use.

In operation, the CPU coordinates the use of the various input and output devices, coordinates data accesses from the mass storage and accesses to and from working memory, and determines the sequence of data processing steps. A number of programs may be used to process the machine-readable data of this invention, including commercially-available software.

A magnetic storage medium for storing machine-readable data according to the invention can be conventional. A magnetic data storage medium can be encoded with a machine-readable data that can be carried out by a system such as the computer system described above. The medium can be a conventional floppy diskette or hard disk, having a suitable substrate which may be conventional, and a suitable coating, which may also be conventional, on one or both sides, containing magnetic domains whose polarity or orientation can be altered magnetically. The medium may also have an opening (not shown) for receiving the spindle of a disk drive or other data storage device.

The magnetic domains of the medium are polarized or oriented so as to encode in a manner which may be conventional, machine readable data such as that described herein, for execution by a system such as the computer system described herein.

An optically-readable data storage medium also can be encoded with machine-readable data, or a set of instructions, which can be carried out by a computer system. The medium can be a conventional compact disk read only memory (CD-ROM) or a rewritable medium such as a magneto-optical disk which is optically readable and magneto-optically writable.

In the case of CD-ROM, as is well known, a disk coating is reflective and is impressed with a plurality of pits to encode the machine-readable data. The arrangement of pits is read by reflecting laser light off the surface of the coating. A protective coating, which preferably is substantially transparent, is provided on top of the reflective coating.

In the case of a magneto-optical disk, as is well known, a data-recording coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Structure data, when used in conjunction with a computer programmed with software to translate those coordinates into the 3-dimensional structure of a molecule or molecular complex comprising an APC binding site may be used for a variety of purposes, such as drug discovery.

For example, the structure encoded by the data may be computationally evaluated for its ability to associate with chemical entities. Chemical entities that associate with a binding site of a pol-β protein are expected to be toxic to neoplastic cells (e.g., glioblastoma, lung cancer, colon cancer cells), to inhibit base excision repair, or to enhance the efficacy of an alkylating agent. Such compounds are potential drug candidates. Alternatively, the structure encoded by the data may be displayed in a graphical three-dimensional representation on a computer screen. This allows visual inspection of the structure, as well as visual inspection of the structure's association with chemical entities.

Thus, using computational methods it is possible to evaluate the potential of a chemical entity to associate with a) a molecule or molecular complex comprising a binding site defined by structure coordinates of pol-β, as described herein, or b) a homologue of said molecule or molecular complex, wherein said homologue comprises a binding pocket that has a root mean square deviation from the backbone atoms of said amino acids of not more than 2.0 (more preferably 1.5) angstroms.

Such a method may comprises the steps of:

i) employing computational means to perform a fitting operation between the chemical entity and a binding site of the pol-β polypeptide or fragment thereof or molecular complex; and ii) analyzing the results of the fitting operation to quantify the association between the chemical entity and the APC binding site. This embodiment relates to evaluating the potential of a chemical entity to associate with or bind to a binding site of a pol-β polypeptide or fragment thereof.

The term "chemical entity", as used herein, refers to chemical compounds, complexes of at least two chemical compounds, and fragments of such compounds or complexes.

Such a method may also be used to evaluate the potential of a chemical entity to associate with a molecule or molecular complex defined by structure coordinates of all of the amino acids of pol-β protein, as described herein, or a homologue of said molecule or molecular complex having a root mean square deviation from the backbone atoms of said amino acids of not more than 2.0 (more preferably not more than 1.5) angstroms.

Additionally, using computational methods the structural coordinates of one of the binding sites described herein can be utilized in a method for identifying an antagonist of a molecule comprising a APC binding site (e.g., a binding site within the pol-β sequence). This method comprises the steps of:

a) using the atomic coordinates of pol-β;

b) employing the three-dimensional structure to design or select the potential agonist or antagonist. The method further includes the optional steps of c) synthesizing the agonist or antagonist; and d) contacting the agonist or antagonist with the molecule to determine the ability of the potential agonist or antagonist to interact with the molecule. If desired, the method further involves the step of contacting a neoplastic cell (e.g., glioblastoma cell) with a pol-β binding compound and evaluating cytotoxicity in the presence or the absence of an alkylating agent, evaluating neoplastic cell proliferation, cell death, or BER activity.

Additionally, using computational methods it is possible to identify a potential antagonist of pol-β polypeptide, comprising the steps of:

a) using the atomic coordinates of the pol-β polypeptide (e.g., APC binding site sequence, including at least about Thr79, Lys81 and Arg83 amino acid residues of Pol-β, or other residues that mediate the interaction of Pol-β with APC); and b) employing the three-dimensional structure to design or select the potential antagonist.

Knowledge of the APC binding site of a pol-β polypeptide provides the necessary information for designing new chemical entities and compounds that may interact with pol-β proteins, in whole or in part, and may therefore modulate (e.g., inhibit) the activity of pol-β proteins.

The design of compounds that bind to a pol-β sequence, that are cytotoxic to a neoplastic cell, or that reduce pol-β expression or biological activity, according to this invention generally involves consideration of several factors. In one embodiment, the compound physically and/or structurally associates with at least a fragment of a pol-β polypeptide, such as an APC binding site within a pol-β sequence. Non-covalent molecular interactions important in this association include hydrogen bonding, van der Waals interactions, hydrophobic interactions and electrostatic interactions. Desirably, the compound assumes a conformation that allows it to associate with the APC binding site(s) directly. Although certain portions of the compound may not directly participate in these associations, those portions of the entity may still influence the overall conformation of the molecule. This, in turn, may have a significant impact on the compound's potency. Such conformational requirements include the overall three-dimensional structure and orientation of the chemical compound in relation to all or a portion of the binding site, or the spacing between functional groups comprising several chemical compound that directly interact with the binding site or a homologue thereof.

The potential inhibitory or binding effect of a chemical compound on a pol-β APC binding site may be analyzed prior to its actual synthesis and testing by the use of computer modeling techniques. If the theoretical structure of the given compound suggests insufficient interaction and association between it and the target binding site, testing of the compound is obviated. However, if computer modeling indicates a strong interaction, the molecule is synthesized and tested for its ability to bind a pol-β sequence or to test its biological activity by assaying for example, cytotoxicity in a neoplastic cell, by assaying an increase in the efficacy of an alkylating agent in a neoplastic cell. Candidate compounds may be computationally evaluated by means of a series of steps in which chemical entities or fragments are screened and selected for their ability to associate with the APC binding site.

One skilled in the art may use one of several methods to screen chemical compounds, or fragments for their ability to associate with a APC binding site. This process may begin by visual inspection of, for example, a APC binding site on the computer screen based on the a pol-β structure coordinates described herein, or other coordinates which define a similar shape generated from the machine-readable storage medium. Selected fragments or chemical compounds are then positioned in a variety of orientations, or docked, within that binding site as defined supra. Docking may be accomplished using software such as Quanta and DOCK, followed by energy minimization and molecular dynamics with standard molecular mechanics force fields, such as CHARMM and AMBER.

Specialized computer programs (e.g., as known in the art and/or commercially available and/or as described herein) may also assist in the process of selecting fragments or chemical entities.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of the target binding site.

Instead of proceeding to build an inhibitor of a binding pocket in a step-wise fashion one fragment or chemical entity at a time as described above, inhibitory or other binding compounds may be designed as a whole or "de novo" using either an empty binding site or optionally including some portion(s) of a known inhibitor(s). There are many de novo ligand design methods known in the art, some of which are commercially available (e.g., LeapFrog, available from Tripos Associates, St. Louis, Mo.).

Other molecular modeling techniques may also be employed in accordance with this invention (see, e.g., N. C. Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)).

Once a compound has been designed or selected, the efficiency with which that entity may bind to a binding site may be tested and optimized by computational evaluation.

Specific computer software is available in the art to evaluate compound deformation energy and electrostatic interactions. Examples of programs designed for such uses include: AMBER; QUANTA/CHARMM (Accelrys, Inc., Madison, Wis.) and the like. These programs may be implemented, for instance, using a commercially-available graphics workstation. Other hardware systems and software packages will be known to those skilled in the art.

Another technique for identifying pol-β inhibitors involves the in silico screening of virtual libraries of compounds, e.g., as described herein (see, e.g., Examples). Many thousands of compounds can be rapidly screened and the best virtual compounds can be selected for further screening (e.g., by synthesis and in vitro or in vivo testing). Small molecule databases can be screened for chemical entities or compounds that can bind, in whole or in part, to an APC binding site. In this screening, the quality of fit of such entities to the binding site may be judged either by shape complementarity or by estimated interaction energy.

Using computational methods to identify pol-β inhibitors, one of skill in the art may produce a three-dimensional representation of
a) a molecule or molecular complex, wherein said molecule or molecular complex comprises a binding site in the linker sequence of a pol-β polypeptide defined by structure coordinates of amino acid residues in the APC binding site; or
b) a three-dimensional representation of a homologue of said molecule or molecular complex, wherein said homologue comprises a binding site that has a root mean square deviation from the backbone atoms of said amino acids of not more than about 2.0 (more preferably not more than 1.5) angstroms. Such a computer may comprise:
(i) a machine-readable data storage medium comprising a data storage material encoded with machine-readable data, wherein said data comprises the structure coordinates of structure coordinates of amino acid residues in the APC binding site of a pol-β polypeptide;
(ii) a working memory for storing instructions for processing said machine-readable data;
(iii) a central-processing unit coupled to said working memory and to said machine-readable data storage medium for processing said machine readable data into said three-dimensional representation; and
(iv) a display coupled to said central-processing unit for displaying said three-dimensional representation. As described in the Examples, compounds identified using in silico methods may optionally be tested in vitro or in vivo, for example, using the "Additional Screening Methods" described below, or any other method known in the art.

Additional Screening Methods

As described above, the invention provides specific examples of chemical compounds that are cytotoxic to neoplastic cells when administered alone or in combination with an alkylating agent. However, the invention is not so limited. The invention further provides a simple means for identifying agents (including nucleic acids, peptides, small molecule inhibitors, and mimetics) that are capable of binding to a pol-β polypeptide, for example, binding to an APC binding site, and that are cytotoxic to a neoplastic cell, particularly when administered in combination with an akylating agent or other chemotherapeutic. Such compounds are also expected to be useful for the treatment or prevention of a neoplasia (e.g., breast cancer, colon cancer, glioblastoma, lung cancer).

In particular, because agents that bind to pol-β at an APC binding site reduce the activity of a BER pathway, such agents are likely useful as therapeutics for the treatment or prevention of a neoplasia.

Virtually any agent that specifically binds to a pol-β polypeptide and that reduces BER activity may be employed in the methods of the invention. Methods of the invention are useful for the high-throughput low-cost screening of candidate agents that reduce, slow, or stabilize the growth or proliferation of a neoplasia. A candidate agent that specifically binds to pol-β is then isolated and tested for activity in an in vitro assay or in vivo assay for its ability to reduce neoplastic cell proliferation, increase the efficacy of an alkylating agent, and/or increase neoplastic cell death. One skilled in the art appreciates that the effects of a candidate agent on a cell is typically compared to a corresponding control cell not contacted with the candidate agent. Thus, the screening methods include comparing the proliferation of a neoplastic cell contacted by a candidate agent to the proliferation of an untreated control cell.

In other embodiments, the expression or activity of pol-β in a cell treated with a candidate agent is compared to untreated control samples to identify a candidate compound that decreases the expression or biological activity of a pol-β polypeptide in the contacted cell. Polypeptide expression or activity can be compared by procedures well known in the art, such as Western blotting, flow cytometry, immunocytochemistry, binding to magnetic and/or pol-β-specific antibody-coated beads, in situ hybridization, fluorescence in situ hybridization (FISH), ELISA, microarray analysis, RT-PCR, Northern blotting, or colorimetric assays, such as the Bradford Assay and Lowry Assay.

In one working example, one or more candidate agents are added at varying concentrations to the culture medium containing a neoplastic cell. An agent that binds in an APC binding site of pol-β or that reduces the expression or activity of a pol-β protein expressed in the cell is considered useful in the invention; such an agent may be used, for example, as a therapeutic to prevent, delay, ameliorate, stabilize, or treat a neoplasia. Once identified, agents of the invention (e.g., agents that specifically bind to and/or antagonize pol-β) may be used to treat a neoplasia. An agent identified according to a method of the invention is locally or systemically delivered to treat a neoplasia in situ.

If one embodiment, the effect of a candidate agent may, in the alternative, be measured at the level of pol-β polypeptide production using the same general approach and standard immunological techniques, such as Western blotting or immunoprecipitation with an antibody specific for pol-β. For example, immunoassays may be used to detect or monitor the expression of pol-β in a neoplastic cell. In one embodiment, the invention identifies a polyclonal or monoclonal antibody (produced as described herein) that is capable of binding to a pol-β APC binding site and reducing the biological activity of a pol-β polypeptide. A compound that reduces the expression or activity of a pol-β polypeptide is considered particularly useful. Again, such an agent may be used, for example, as a therapeutic to prevent or treat a neoplasia.

Alternatively, or in addition, candidate compounds may be identified by first assaying those that specifically bind to and antagonize a pol-β polypeptide of the invention and subsequently testing their effect on neoplastic cells as described in the Examples. In one embodiment, the efficacy of a candidate agent is dependent upon its ability to interact with the pol-β polypeptide. Such an interaction can be readily assayed using any number of standard binding techniques and functional assays (e.g., those described in Ausubel et al., supra). For example, a candidate compound may be tested in vitro for interaction and binding with a polypeptide of the invention and its ability to modulate neoplastic cell proliferation may be assayed by any standard assays (e.g., those described herein). In one embodiment, division of neoplastic cells is determined by assaying BrdU incorporation using flow cytometry analysis. In another embodiment, pol-β expression is monitored immunohistochemically.

Potential pol-β antagonists include organic molecules, peptides, peptide mimetics, polypeptides, nucleic acid ligands, aptamers, and antibodies that bind to a pol-β polypeptide and reduce its activity. In one particular example, a candidate compound that binds to a pol-β polypeptide may be identified using a chromatography-based technique. For example, a recombinant pol-β polypeptide of the invention may be purified by standard techniques from cells engineered to express the polypeptide, or may be chemically synthesized, once purified the peptide is immobilized on a column. A solution of candidate agents is then passed through the column, and an agent that specifically binds the pol-β polypeptide or a fragment thereof is identified on the basis of its ability to bind to pol-β polypeptide and to be immobilized on the column. To isolate the agent, the column is washed to remove non-specifically bound molecules, and the agent of interest is then released from the column and collected. Agents isolated by this method (or any other appropriate method) may, if desired, be further purified (e.g., by high performance liquid chromatography). In addition, these candidate agents may be tested for their ability to reduce neoplastic cell proliferation or viability. Agents isolated by this approach may also be used, for example, as therapeutics to treat or prevent a neoplasia. Compounds that are identified as binding to a pol-β polypeptide with an affinity constant less than or equal to 1 nM, 5 nM, 10 nM, 100 nM, 1 µM or 10 µM are considered particularly useful in the invention.

Test Compounds and Extracts

In general, pol-β antagonists (e.g., agents that specifically bind and reduce the activity of a pol-β polypeptide) and other agents that enhance the efficacy of an agent described herein are identified from large libraries of natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Agents used in screens may include known those known as therapeutics for the treatment of a neoplasia. Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as the modification of existing polypeptides.

Libraries of natural polypeptides in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Such polypeptides can be modified to include a protein transduction domain using methods known in the art and described herein. In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994. Furthermore, if desired, any library or compound is readily modified using standard chemical, physical, or biochemical methods.

Numerous methods are also available for generating random or directed synthesis (e.g., semi-synthesis or total synthesis) of any number of polypeptides, chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Libraries of compounds may be presented in solution (e.g., Houghten, *Biotechniques* 13:412-421, 1992), or on beads (Lam, *Nature* 354:82-84, 1991), chips (Fodor, *Nature* 364:555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222:301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is found to have pol-β binding activity further fractionation of the positive lead extract is necessary to isolate molecular constituents responsible for the observed effect. Thus, the goal of the extraction, fractionation, and purification process is the careful characterization and identification of a chemical entity within the crude extract that reduces neoplastic cell proliferation or viability. Methods of fractionation and purification of such heterogenous extracts are known in the art. If desired, compounds shown to be useful as therapeutics are chemically modified according to methods known in the art.

Pharmaceutical Therapeutics

In other embodiments, agents discovered to have medicinal value using the methods described herein are useful as a drug or as information for structural modification of existing compounds, e.g., by rational drug design. Such methods are useful for screening agents having an effect on a neoplasia.

For therapeutic uses, the compositions or agents identified using the methods disclosed herein may be administered systemically, for example, formulated in a pharmaceutically-acceptable buffer such as physiological saline. Preferable routes of administration include, for example, subcutaneous, intravenous, interperitoneally, intramuscular, or intradermal injections that provide continuous, sustained levels of the drug in the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia. Generally, amounts will be in the range of those used for other agents used in the treatment of other diseases associated with neoplasia, although in certain instances lower amounts will be needed because of the increased specificity of the compound. A compound is administered at a dosage that is cytotoxic to a neoplastic cell, that reduces pol-β expression or biological activity, or that reduces the proliferation, survival, or invasiveness of a neoplastic cell as determined by a method known to one skilled in the art, or using any that assay that measures the expression or the biological activity of a pol-β polypeptide.

Formulation of Pharmaceutical Compositions

The administration of a compound or a combination of compounds for the treatment of a neoplasia may be by any suitable means that results in a concentration of the therapeutic that, combined with other components, is effective in ameliorating, reducing, or stabilizing a neoplasia. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 μg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other embodiments, it is envisaged that doses may be in the range of about 5 mg compound/Kg body to about 20 mg compound/Kg body weight. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that target a neoplasia by using carriers or chemical derivatives to deliver the therapeutic agent to a particular cell type (e.g., neoplastic cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a neoplasia, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active antineoplastic therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug may be incorporated in biocompatible carriers, liposomes, nanoparticles, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Solid Dosage Forms for Oral Use

Formulations for oral use include tablets containing the active ingredient(s) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

The solid tablet compositions may include a coating adapted to protect the composition from unwanted chemical changes, (e.g., chemical degradation prior to the release of the active anti-neoplasia therapeutic substance). The coating may be applied on the solid dosage form in a similar manner as that described in Encyclopedia of Pharmaceutical Technology, supra.

At least two anti-neoplasia therapeutics may be mixed together in the tablet, or may be partitioned. In one example, the first active anti-neoplasia therapeutic is contained on the inside of the tablet, and the second active anti-neoplasia therapeutic is on the outside, such that a substantial portion of the second anti-neoplasia therapeutic is released prior to the release of the first anti-neoplasia therapeutic.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms

Controlled release compositions for oral use may, e.g., be constructed to release the active anti-neoplasia therapeutic by controlling the dissolution and/or the diffusion of the active substance. Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more therapeutic compounds may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the compound(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

The present invention provides methods of treating neoplastic disease and/or disorders or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a neoplastic disease or disorder or symptom thereof. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a neoplastic disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which pol-β may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with neoplasia in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Selection of a Treatment Method

After a subject is diagnosed as having a neoplasia (e.g., breast cancer) a method of treatment is selected. In breast cancer, for example, a number of standard treatment regimens are available. The hormone responsiveness profile of the breast cancer is used in selecting an appropriate treatment method. The expression of hormone/growth factor receptors can be divided into three groups: (i) Estrogen receptor (ER) and progesterone receptor (PR)-positive; (ii) Human epidermal growth factor receptor 2 (HER2)-positive; and (iii) ER, PR, and HER2-negative (triple-negative). In generaly, triple-negative breast cancers are more aggressive, and are less susceptible to conventional treatment methods. For triple-negative breast tumors, few therapeutic options are available, and such tumors often correlate with poor clinical outcomes, such as metastasis or death. A subject having a triple-negative breast tumor is identified as likely to benefit from treatment with a composition of the invention comprising temozolomide, NSC-124854 or NSC-666715, and $O^6$ benzyl guanine or curcumin. Thus, the invention provides methods for selecting a therapy for a subject, the method involving identifying a subject as having a triple-negative breast tumor, and administering to the subject a therapeutic combination of the invention.

ER/PR/HER2-responsive tumors are more likely to correlate with good clinical outcomes. Nevertheless, a subject identified as having a ER/PR/HER2-responsive tumor is also likely to benefit from treatment with the methods of the invention. Accordingly, the invention provides methods for selecting a therapy for a subject, the method involving identifying a subject as having a ER/PR/HER2-responsive tumor, and administering to the subject a therapeutic combination of the invention. When methods of the invention indicate that a neoplasia is very aggressive, an aggressive method of treatment should be selected. Aggressive therapeutic regimens typically include one or more of the following therapies: radical mastectomy, radiation therapy, hormone therapy, and chemotherapy. Such methods may be used in combination with the therapeutic methods described herein, particularly for the treatment of triple-negative breast cancer, which is prone to relapse.

Methods of Treatment

In one embodiment, the present invention provides a method of treating breast cancer (e.g., ER/PR/HER2-responsive tumor or a triple-negative breast cancer). Advantageously, the invention provides methods for treating breast cancers that are less susceptible to conventional treatment methods. The methods involve administering to a subject having a neoplasia an effective amount of a therapeutic combination of the invention. For example, a composition comprising an alkylating agent, such as temozolomide, a small molecule inhibitor, such as NSC-666715 or NSC-124854, together with $O^6$ benzylguanine or a chemopreventive agent, such as curcumin. Preferably, such agents are administered as part of a composition additionally comprising a pharmaceutically acceptable carrier. Preferably this method is employed to treat a subject suffering from or susceptible to a neoplasia. Other embodiments include any of the methods herein wherein the subject is identified as in need of the indicated treatment.

Another aspect of the invention is the use of a combination of the invention in the manufacture of a medicament for treating a neoplasia (e.g., ER/PR/HER2-responsive tumor or triple-negative breast cancer) in a subject. Preferably, the medicament is used for treatment or prevention in a subject of a disease, disorder or symptom set forth above.

Kits or Pharmaceutical Systems

The present compositions may be assembled into kits or pharmaceutical systems for use in ameliorating a neoplasia. Kits or pharmaceutical systems according to this aspect of the invention comprise a carrier means, such as a box, carton, tube or the like, having in close confinement therein one or more container means, such as vials, tubes, ampoules, bottles and the like. The kits or pharmaceutical systems of the invention may also comprise associated instructions for using the agents of the invention. Kits of the invention include at least one or more alkylating agents (e.g., temozolomide, and at least one or more agents that bind to an APC binding site on pol-β or that reduce pol-β or BER pathway activity (e.g., APC or an APC mimetic, such as NSC-124854 and NSC-666715). If desired, the kit also includes an agent that binds to $O^6$-methylguanine DNA-methyltransferase (MGMT) and reduces MGMT-mediated DNA repair (e.g., $O^6$-benzylguanine) or a chemopreventive agent (e.g., curcumin). The kit may include instructions for administering the alkylating agent in combination with one or more agents that bind to an APC binding site on pol-β or that reduce pol-β or BER pathway activity, thereby increasing the efficacy of the alkylating agent relative to the efficacy of the alkylating agent administered alone. Methods for measuring the efficacy of alkylating agents are known in the art and are described herein (e.g., measuring the $IC_{50}$).

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Structure-Based Docking of NSC666715 and NSC-124854 at Amino Acid Residues T79, K81 and R83 of DNA Polymerase β (Pol-β)

Adenomatous polyposis coli (APC) interacts with Pol-β at amino acid residues T79, K81 and R83 and blocks Pol-β-directed BER (FIGS. 1A and 1B). This site had chemical and geometric characteristics appropriate for binding of small molecule inhibitors. Based on this finding, small molecule inhibitors that mimic the binding of APC with Pol-β were expected to block Pol-β-directed BER. A library of 240,000 agents was screened to identify those that are likely to bind at amino acid residues T79, K81 and R83 of Pol-β and block its activity. By using functional BER assays, NSC-124854 and NSC-666715 were identified (FIGS. 1A and 1B).

Example 2

NSC-124854 and NSC-666715 Block Pol-β-Directed SN- and LP-BER

Figure 2:
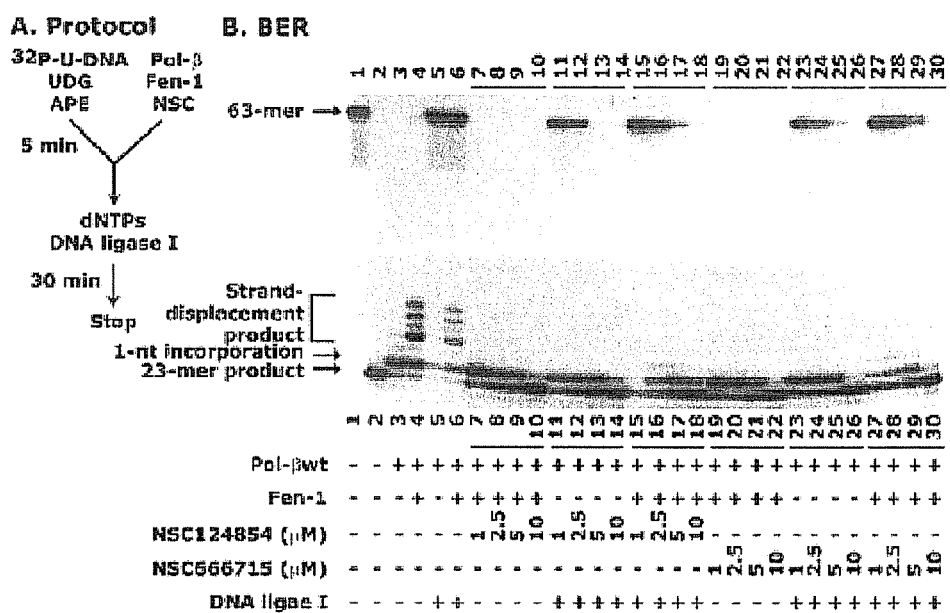
FIGS. 2A and 2B show that NSC-124854 and NSC-666715 block Pol-β-directed single nucleotide and long patch activities. The reaction conditions are described below.

The NSC-124854 and NSC-666715 block Pol-β-directed SN- and LP-BER. An assay was developed that permits in vitro analysis of BER as described in FIG. 2A. While using $^{32}$P-U-DNA as a substrate, both BER sub-pathways—the single nucleotide (SN)- and the long-patch (LP)-BER can be separated by the addition of Fen-1. In the presence of Fen-1, $^{32}$P-U-DNA shows strand-displacement synthesis and the repair takes place through LP-BER. The results showed Pol-β-mediated 1-nt incorporation (FIG. 2B, compare lane 2 with 3) as well as strand-displacement synthesis in the presence of Fen-1 (FIG. 2B, compare lane 2 with 4). The complete repair of DNA by SN- and LP-BER pathways is mediated by DNA ligase I (FIG. 2B, lane 5 and 6, respectively).

Both NSC-124854 and NSC-666715 blocked 1-nt incorporation as well as strand-displacement synthesis in a dose-dependent manner (FIG. 2B, compare lane 4 with 7-10 and lane 4 with 19-22, respectively). Furthermore, the complete repair of $^{32}$P-U-DNA by the SN-BER pathway was blocked by NSC-124854 (FIG. 2B, compare lane 5 with 11-14) and NSC-666715 (FIG. 2B, compare lane 5 with 23-26) in a dose-dependent manner. The complete repair of $^{32}$P-U-DNA by the LP-BER pathway was also blocked in a dose-dependent manner by NSC-124854 (FIG. 2B, compare lane 5 with 15-18) and NSC-666715 (FIG. 2B, compare lane 5 with 27-30). These results support the conclusion that NSC-124854 and NSC-666715 are highly specific inhibitors of Pol-β.

Example 3

NSC-666715 Increased Cytotoxicity of Temozolomide or a Combination of Temozolomide and $O^6$-Benzylguanine in Hormone/Growth Factor Responsive Breast Cancer Cells The cytotoxicity of the majority of chemotherapeutic drugs, as well as of ionizing radiation, is directly related to the drug's ability to cause DNA damage. There are several possible cellular responses to such potentially cytotoxic insults, such as induction of apoptosis, modulation of cell cycle progression, tolerance of damage and initiation of DNA repair. These responses ultimately determine whether the cell is fated to survive with a mutated genome or to die by apoptosis. Responses that promote cell survival have a negative impact on treatment efficacy and lead to resistance to therapies. Thus, agents that increase DNA damage and reduce DNA repair can be an appropriate strategy for cancer treatment. Temozolomide (TMZ) is a DNA-alkylating drug approved for the treatment of glioblastoma (Kim L, Curr. Treat. Options Oncol. 7: 467-478, 2006; Robins et al., Curr. Oncol. Rep. 9: 66-70, 2007). TMZ can cross the blood brain barrier. It is nonenzymatically hydrolyzed in solution to the active compound 3-methyl-(triazen-1-yl)imidazole-4-carboxamide (MTIC). Activated 3-MTIC methylates DNA primarily at the $N^7$ and $O^6$ positions of guanine and the $N^3$ of adenine (70%, 5%, and 9%, respectively). The $O^6$mG is repaired by the $O^6$-methylguanine DNA-methyltransferase (MGMT)/mismatch repair (MMR) pathway. Both $N^7$mG and $N^3$mA lesions of DNA are repaired by the base excision repair pathway. These lesions, if not repaired, can accumulate and cause strand breaks that can lead to apoptosis. $O^6$-benzylguanine is a guanine analog that binds $O^6$-methylguanine DNA-methyltransferase (MGMT). It inhibits MGMT-mediated DNA repair by transferring its benzyl moiety to the active-site cysteine. Because NSC-666715 blocks base excision repair, it is hypothesized that cells treated with NSC-666715 will likely be more sensitive to TMZ and BG due to decreased base excision repair.

Figure 3:
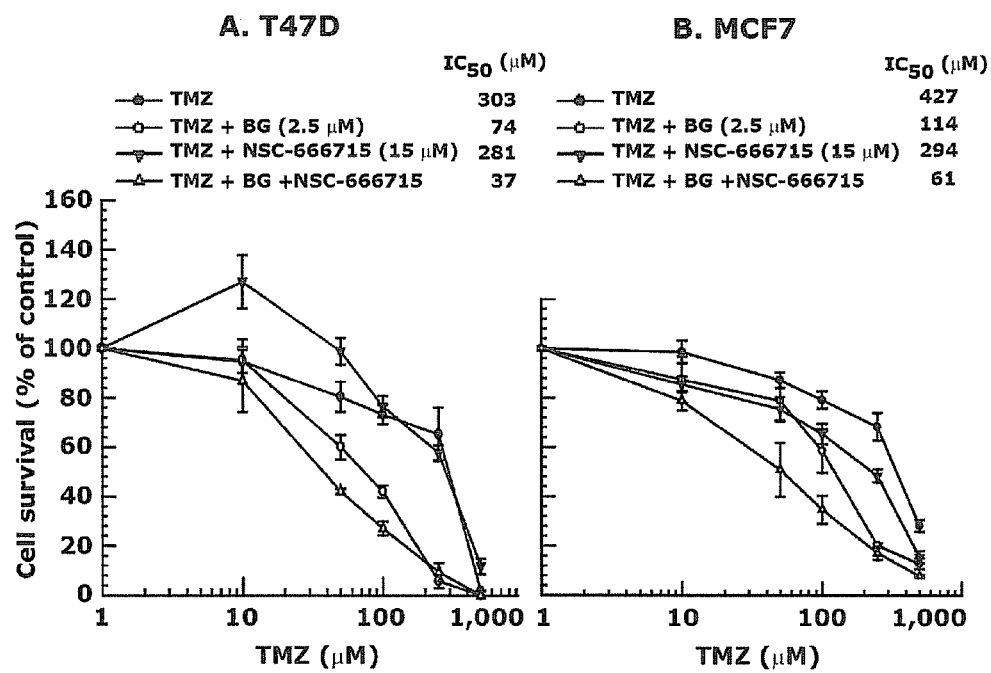
FIGS. 3A and 3B show that BG and NSC-666715 enhanced the cytotoxicity of temozolomide against ER/PR/ HER2-responsive breast cancer cell lines in a clonogenic assay. T47D (ER+/PR+) (FIG. 3A) and MCF7 (ER+/PR+/ HER2+) (FIG. 3B) human breast cancer cell lines were treated different concentrations of Temozolomide (TMZ; 1-1000 µM) alone or in combination with $O^6$-benzylguanine (BG; 2.5 µM) and NSC-666715 (15 µM). After 48 hours, cells were harvested and processed for cytotoxicity determination by clonogenic assay. Data presented are the mean±SE of three different estimations. The insets in FIGS. 3A and 3B show the $IC_{50}$ (µM) of TMZ alone (solid circle), TMZ and BG in combination (open circle), TMZ and NSC-666715 in combination (solid triangle), and TMZ, BG, and NSC-666715 in combination (open triangle). The $IC_{50}$ for BG and NSC-666715 in these cell lines was in the range of 75 and 100 µM, respectively.

The $IC_{50}$ (the drug concentration needed to prevent cell proliferation by 50%) of TMZ was determined using a sulforhodamine B (SRB) colorimetric assay. This assay relies on the ability of SRB to bind the protein components of cells that have been fixed to tissue culture plates by trichloroacetic acid (TCA) (Vachai V, Kirtikara K. Sulforhodamine B colorimetric assay for cytotoxicity screening. Nat. Proto. 3: 1122-1116, 2006). MCF7 and T47D cells were seeded in 96-well plates at a density of 500 cells per well. After 24 hours, while the cells were in the log phase of cell growth, the cells were treated with different concentrations of TMZ (1-1000 μM) for 48 hours. To determine the effect of additional agents on the cytotoxicity of TMZ, TMZ-treated cells were additionally treated with combinations of BG (2.5 μM), NSC-666715 (15 μM), or both BG (2.5 μM) and NSC-666715 (15 μM) (FIG. 3). The cells were subsequently fixed with 10% (w/v) of tricholoroacetic acid, washed with double distilled water, and stained with 0.4% SRB. Cells were then repeatedly washed with 1% (v/v) of acetic acid to remove the unbound dye. The protein bound dye was dissolved in 10 mM Tris-base solution (pH 10.5). The developed color was measured at 564 nm. The percentage of cell survival as a function of drug concentration was then plotted to determine the $IC_{50}$ value.

Figure 5:
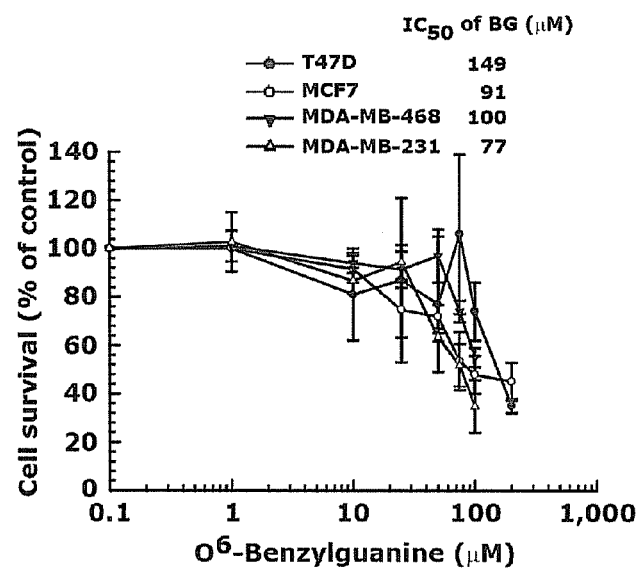
FIG. 5 shows a dose response analysis of $O^6$-benzylguanine (BG) cytotoxicity in T47D, MCF7, MDA-MB468, and MDA-MB-231 breast cancer cell lines. Data from T47D (ER+/PR+), MCF7 (ER+/PR+/HER2+), MDA-MB468 (ER−/ PR−/HER2−), and MDA-MB-231 (ER−/PR−/HER2−) breast cancer cell lines are shown. Data are the mean±SE of three different estimations. The inset shows the $IC_{50}$ (µM) of TMZ in T47D, MCF7, MDA-MB468, and MDA-MB-231 breast cancer cell lines.

NSC-666715 (15 μM) was able to reduce the amount of TMZ required for cytotoxicity of T47D ($ER^+/PR^+/HER2^+$; hormone/growth factor responsive) breast cancer cells as determined by the $IC_{50}$ (FIG. 3A). The $IC_{50}$ of TMZ alone on the cytotoxicity of T47D breast cancer cells was 303 μM. The treatment of T47D cells using TMZ with either BG (2.5 μM) or NSC-666715 (15 μM) reduced the $IC_{50}$ of TMZ by about 4-fold and about 1.1-fold, respectively. By comparison, the $IC_{50}$ of BG was about 149 μM in T47D cells (FIG. 5). Moreover, the treatment of T47D cells by administering TMZ with both BG (2.5 μM) and NSC-666715 (15 μM) reduced the $IC_{50}$ by about 8-fold. This increase in TMZ-mediated cytotoxicity was synergistic, as it was more than would be predicted by the individual effects of the addition of BG or NSC-666715 on TMZ-mediated cytotoxicity in T47D breast cancer cells.

NSC-666715 (15 μM) was able to reduce the amount of TMZ required for cytotoxicity of MCF7 ($ER^+/PR^+$; hormone responsive) breast cancer cells as determined by the $IC_{50}$ (FIG. 3B). The $IC_{50}$ of TMZ alone on the cytotoxicity of MCF7 breast cancer cells was 303 μM. The treatment of MCF7 cells using TMZ with either BG (2.5 μM) or NSC-666715 (15 μM) reduced the $IC_{50}$ of TMZ by about 4-fold and about 1.5-fold, respectively. By comparison, the $IC_{50}$ of BG on MCF7 cells was about 91 μM (FIG. 5). Furthermore, the treatment of MCF7 cells by administering TMZ with both BG (2.5 μM) and NSC-666715 (15 μM) reduced the $IC_{50}$ by about 7-fold. This increase in TMZ-mediated cytotoxicity was synergistic, as it was more than would be predicted by the individual effects of the addition of BG or NSC-666715 on TMZ-mediated cytotoxicity in MCF7 breast cancer cells.

Co-treatment with NSC-666715 and BG reduced the effective amount of TMZ for killing $ER^+/PR^+$ and $ER^+/PR^+/HER2^+$ breast cancer cells. Without wishing to be bound to a particular theory, these results are consistent with cell death caused by increased DNA damage and decreased repair through MGMT and BER DNA repair pathways. Therefore, administration of NSC-666715 with TMZ and BG is likely to be effective for chemotherapy in $ER^+/PR^+$ and $ER^+/PR^+/HER2^+$ breast cancers.

Example 4

NSC-666715 Increases Cytotoxicity of TMZ or a Combination of TMZ and BG in Hormone/Growth Factor Nonresponsive Breast Cancer Cells In contrast to $ER^+/PR^+$ and $ER^+/PR^+/HER2^+$ breast cancers, there are no specific treatment guidelines to manage $ER^-/PR^-/HER2^-$ breast cancers (i.e., hormone/growth factor nonresponsive or triple-negative). Typically, hormone/growth factor nonresponsive breast cancers are managed with standard combinatorial treatment (e.g., platinum drugs and taxanes with anthracycline, doxorubicin, or epirubicin), which are associated with a high rate of local and systemic relapse. To determine whether NSC-666715 would also increase cytotoxicity of TMZ or a combination of TMZ and BG in hormone/growth factor nonresponsive breast cancer cells, cellular toxicity was determined by sulforhodamine B (SRB) colorimetric assay as described above on MDA-MB-468 and MDA-MB-231 breast cancer cell lines.

Figure 4:
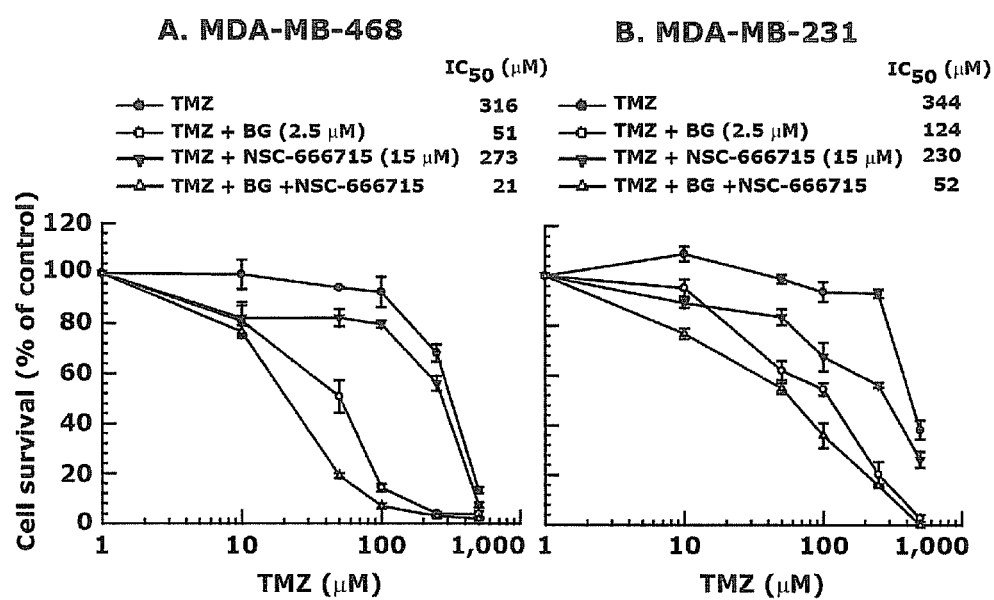
FIGS. 4A and 4B show that NSC-666715 enhanced the cytotoxicity of TMZ and TMZ and BG in combination in two hormone/growth factor-negative (ER−/PR−/HER−) breast cancer cell lines in culture. MDA-MB468 (ER−/PR−/HER2−) (FIG. 4A) and MDA-MB-231 (ER−/PR−/HER2−) (FIG. 4B) human breast cancer cell lines were treated different concentrations of Temozolomide (TMZ; 1-1000 µM) alone or in combination with $O^6$-benzylguanine (BG; 2.5 µM) and NSC-666715 (15 µM). After 48 hours, drugs were withdrawn and allowed to grow in fresh medium for determination of cytotoxicity by clonogenic assay. Data presented are the mean±SE of three different estimations. The insets in FIGS. 5A and 5B show the $IC_{50}$ (µM) of TMZ alone (solid circle), TMZ and BG in combination (open circle), TMZ and NSC-666715 in combination (solid triangle), and TMZ, BG, and NSC-666715 in combination (open triangle). Data presented are the mean+/−SE of three different estimations. The $IC_{50}$ for BG and NSC-666715 in these cell lines was in the range of 75 and 100 µM, respectively.

The results of this assay showed that NSC-666715 increased the cytotoxicity of TMZ in two hormone/growth factor nonresponsive breast cancer cell lines. NSC-666715 (15 μM) was able to reduce the amount of TMZ required for cytotoxicity of MDA-MB-468 ($ER^-/PR^-/HER2^-$; hormone nonresponsive) breast cancer cells as determined by the $IC_{50}$ (FIG. 4A). The $IC_{50}$ of TMZ alone on the cytotoxicity of MDA-MB-468 breast cancer cells was 316 μM. The treatment of MDA-MB-468 cells using TMZ with either BG (2.5 μM) or NSC-666715 (15 μM) reduced the $IC_{50}$ of TMZ by about 6-fold and about 0.1-fold, respectively. By comparison, the $IC_{50}$ of BG on MDA-MB-468 cells was about 100 μM (FIG. 5). Furthermore, the treatment of MDA-MB-468 cells by administering TMZ with both BG (2.5 μM) and NSC-666715 (15 μM) reduced the $IC_{50}$ by about 15-fold. This increase in TMZ-mediated cytotoxicity was synergistic, as it was more than would be predicted by the individual effects of the addition of BG or NSC-666715 on TMZ-mediated cytotoxicity in MDA-MB-468 breast cancer cells.

NSC-666715 (15 μM) was able to reduce the amount of TMZ required for cytotoxicity of MDA-MB-231 ($ER^-/PR^-/HER2^-$; hormone/growth factor nonresponsive) breast cancer cells as determined by the $IC_{50}$ (FIG. 4B). The $IC_{50}$ of TMZ alone on the cytotoxicity of MDA-MB-231 breast cancer cells was 344 μM. The treatment of MDA-MB-231 cells using TMZ with either BG (2.5 μM) or NSC-666715 (15 μM) reduced the $IC_{50}$ of TMZ by about 2.8-fold and about 1.5-fold, respectively. By comparison, the $IC_{50}$ of BG was about 77 μM in MDA-MB-231 cells (FIG. 5). Moreover, the treatment of MDA-MB-231 cells by administering TMZ with both BG (2.5 μM) and NSC-666715 (15 μM) reduced the $IC_{50}$ by about 6.6-fold. This increase in TMZ-mediated cytotoxicity was synergistic, as it was more than would be predicted by the individual effects of the addition of BG or NSC-666715 on TMZ-mediated cytotoxicity in MDA-MB-231 breast cancer cells.

Co-treatment with NSC-666715 and BG reduced the effective amount of TMZ for cytotoxicity in two $ER^-/PR^-/HER2^-$ breast cancer cell lines. Without wishing to be bound to a particular theory, these results are also consistent with cell death caused by increased DNA damage and decreased repair through MGMT and BER DNA repair pathways. Therefore, administration of NSC-666715 with TMZ and BG is likely to be effective for chemotherapy regardless of whether the breast cancer is hormone/growth factor responsive ($ER^+/PR^+$ and $ER^+/PR^+/HER2^+$) or hormone/growth factor nonresponsive ($ER^-/PR^-/HER2^-$).

Figure 7:
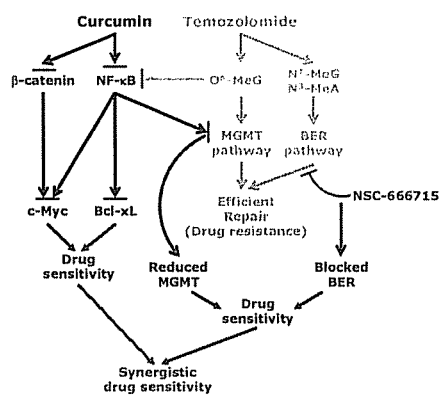
FIG. 7 is a schematic representation showing the interaction of Temozolomide, small molecular weight inhibitors (SMIs) of Pol-β, and curcumin-induced signaling pathways in the attenuation of breast cancer growth.

The following examples, describe results of studies using the structure-based small molecule inhibitors NSC-666715 and NSC-124854 to block DNA repair pathway(s). The chemotherapeutic drugs that induce DNA-alkylation damage are primarily repaired by the BER pathway. As reported in more detail below, the efficacy of such drugs was increased by blocking the repair of DNA damage induced by these drugs. Simultaneously, curcumin was used to block MGMT and bcl-xL (anti-apoptotic) gene expression through the NF-κB pathway and c-myc gene expression through the β-catenin/Tcf-Lef and NF-κB pathways. The interaction of DNA repair and different signaling pathways are illustrated in FIG. 7.

Example 5

The Cytotoxic Effect of TMZ on ER/PR/HER2-Positive and Triple-Negative Breast Tumors is Enhanced by NSC-666715

TMZ is a DNA-alkylating drug that has been approved for the treatment of glioblastoma. TMZ methylates DNA primarily at the $N^7$ and $O^6$ positions of guanine and the $N^3$ position of adenine (70%, 5%, and 9%, respectively) (Mutter et al., Expert Rev. Anticancer Ther. 6: 1187-1204, 2006; Kaina et al., DNA Repair 6: 1079-1099, 2007). The $N^7$-MeG and $N^3$-MeA lesions are repaired by the BER pathway. The accumulation of these lesions can cause strand breaks that can lead to apoptosis. Under certain circumstances, nucleotide excision repair (NER) can also repair $N^7$-MeG and $N^3$-MeA lesions. Since the NSC-666715 blocks BER, breast cancer cells treated with this SMI could be more sensitive to TMZ treatment due to the SMI-induced reduction in BER. Simultaneously, if the repair of $O^6$-MeG occurs by MGMT, NF-κB, and β-catenin/Tch-Lef pathways and can be blocked by curcumin, then the curcumin and NSC-666715 would synergize the sensitivity of breast cancer cells to TMZ treatment.

Figure 8:
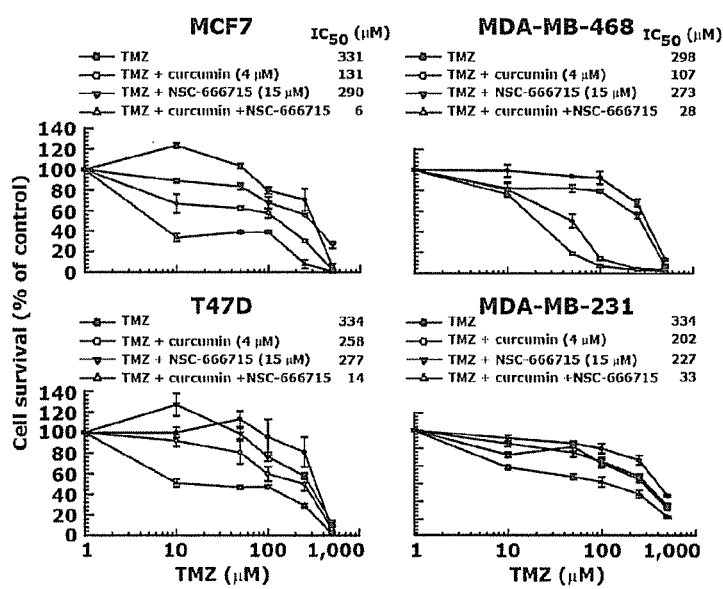
FIG. 8 includes four graphs showing the efficacy of NSC-666715 in enhancing the cytotoxicity of TMZ against ER/PR/ HER2-responsive and triple-negative breast cancer cell lines in culture. Each of the indicated cell cultures were treated with different concentrations of TMZ alone or combination with curcumin and NSC-666715. After 48 hours, drugs were withdrawn and allowed to grow in fresh medium for determination of cytotoxicity by clonogenic assay. The data presented are the mean±SE of three different estimations. The $IC_{50}$ of curcumin and NSC-666715 for these cell lines was 5 and 100 µM, respectively.

To test this hypothesis, the $IC_{50}$ of TMZ in four human breast cancer cell lines was determined using a clonogenic assay (Vachai et al., Nat. Proto. 3: 1122-1116, 2006). The cell lines used were MCF7, T47D (both ER/PR/HER2-positive), MDA-MB-231 and MDA-MB-468 (both triple-negative). The $IC_{50}$ of TMZ alone was 331, 334, 298 and 334 μM in MCF7, T47D, MDA-MB-468 and MDA-MB-231 cells, respectively (FIG. 8). The $IC_{50}$ of TMZ+NSC-666715 was 290, 277, 273 and 227 μM in MCF7, T47D, MDA-MB-468 and MDA-MB-231 cells, respectively. The $IC_{50}$ of TMZ+curcumin was 131, 258, 107 and 202 μM in MCF7, T47D, MDA-MB-468 and MDA-MB-231 cells, respectively. Notably, the $IC_{50}$ of TMZ+curcumin+NSC-666715 was 6, 14, 28 and 33 μM in MCF7, T47D, MDA-MB-468 and MDA-MB-231 cells, respectively, which represent a 55- to 10-fold reduction in the $IC_{50}$ of TMZ when used alone. These results indicated that NSC-666715 in combination with curcumin was able to synergistically increase the cytotoxicity of TMZ and indicated that this effect occurred in both ER/PR/HER2-responsive and triple-negative breast cancer cell lines.

Thus, these results indicate that the SMIs identified herein bind Pol-β at amino acid residues Thr79, Lys81 and Arg83 and block Pol-β-directed BER. Importantly, curcumin can potentiate the chemotherapeutic activity of TMZ, most likely through the regulation of multiple signaling pathways. These results indicate that the combination of SMIs and curcumin will likely serve as a novel strategy for the chemotherapeutic treatment of breast cancers.

Example 6

In Vivo Analysis

The chemosensitivity pattern of TMZ, NSC-666715 and curcumin on the growth of breast cancer cells is evaluate in vivo using an orthotopic xenograft tumor model injected with ER/PR/HER2-responsive (BT474 and MCF7) and three triple-negative (BT20, MDA-MB-231 and MDA-MB-468) breast cancer cell lines. Female SCID mice (25 g body weight) are available from the Charles River Laboratories, Wilmington, Mass. The tumor cells ($5 \times 10^6$ per site) are injected orthotopically in the mammary fat pad as a 1:1 mixture with Matrigel matrix (BD Biosciences, San Diego, Calif.). When the volume of tumor nodules reaches 100-150 $mm^3$ in size, mice are randomly assigned to the control or treatment groups (10 mice/group) as follows: i) vehicle control, ii) TMZ, iii) NSC-666715, iv) curcumin, v) TMZ+NSC-666715, vi) TMZ+curcumin, and vii) TMZ+NSC-666715+curcumin. The mice are treated with TMZ and NSC (intraperitoneally, i.p.) and with curcumin (orally, p.o.). The doses selected are lower than those that have been used previously in animal or clinical trial studies: TMZ—i.p., 15 mg/kg body weight in combination with NSC-666715—i.p., 5 mg/kg body weight (FIG. 8) for five consecutive days, and curcumin—p.o., 500 mg/kg body weight, which is a much lower dose than is recommended in clinical trails. One week later the treatment regimen is repeated and the tumor growth is monitored for four-six weeks depending upon the growth of tumors in control groups without any morbidity. For administration, TMZ and NSC-666715 are freshly dissolved in dimethylsulfoxide immediately prior to use, diluted in 0.9% NaCl solution and injected within 15 minutes. Curcumin is mixed with the Teklad-2019 rodent diet (Harlan, Indianapolis, Ind.) and fed ad libitum. The control group receives the same volume of the vehicle solution.

The biologic effects of TMZ, NSC-666715 and curcumin on the tumor size is evaluated once the tumor reaches about 100-150 $mm^3$. The animals are divided into seven groups. One group receives vehicle control and the other groups receive TMZ, NSC-666715 and curcumin (either alone or in combination) as described above for five days. Tumors are harvested before they regress and processed for analysis of the protein levels of β-catenin, MGMT, c-Myc, and Bcl-xL; the DNA-binding activity of β-catenin/Lef-Tcf, NF-κB; and the mRNA levels of MGMT, c-myc and bcl-xL. This experiment establishes the role of NSC-666715 and curcumin in synergistically enhancing efficacy of TMZ to breast cancer. The results are correlated with tumor size and alterations in the expression of target genes.

Tumor Growth.

Tumor growth is measured with calipers on a daily basis and calculated using the formula: $V = L (mm) \times I^2 (mm)/2$, where V is the volume, L is the largest diameter, and I is the perpendicular diameter of the tumor. The tumors are weighed after the mice have been sacrificed at the termination of the experiment.

Immunohistochemical Analysis.

Sections obtained from the paraffin-embedded tumors will be analyzed using the TUNEL assay to identify apoptotic cells. If rapid tumor regression is observed, tumors are harvested from two or three mice per group prior to complete regression of the tumors to determine apoptotic activity.

In Vivo Toxicity Assay.

Drug toxicity is determined in non-tumor bearing mice in terms of body weight measurements and peripheral WBC counts. Body weight is measured three times weekly from the first treatment until two weeks after the last treatment. The weight loss is expressed as a percentage of the initial weight (initial weight–lowest weight/initial weight×100%). Peripheral WBCs are monitored 5 and 10 days after the end of treatment as compared with WBCs of control mice.

Power Analysis and Statistical Methods.

A statistical analysis of the data is made by comparing the occurrence rate of tumor in each treated group to that in the control group by two-sample binomial test. With 10 mice in each group, a power of 85% is required to detect a difference of 60% in tumor occurrence rate at the 0.05 significance level. If two mice from each group die for reasons unrelated to the tumor study (i.e., eight mice per group), the result will still yield a power of 77% at the 0.05 significance level. The mean of tumor growth in each transformed group is compared to that in the control group by t test.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference. The present application incorporates PCT/US2008/001991 in its entirety.

What is claimed is:

1. A kit for the treatment of breast cancer, the kit comprising temozolomide, O$^6$-benzylguanine or curcumin and NSC-666715 (Benzosulfonamide, 4-chloro-N-[5-[(4-chlorophenyl)amino]1H-1,2,4-triazol-3-yl]-2-mercapto-5-methyl-(9Cl)), and directions for the use of the kit for the treatment of breast cancer.

2. A pharmaceutical composition for the treatment of breast cancer, the composition comprising temozolomide, O$^6$-benzylguanine or curcumin, and NSC-666715 (Benzosulfonamide, 4-chloro-N-[5-[(4-chlorophenyl)amino]1H-1,2,4-triazol-3-yl]-2-mercapto-5-methyl-(9Cl)).

* * * * *

SEQUENCE LISTING

```
<160> NUMBER OF SEQ ID NOS: 2

<210> SEQ ID NO 1
<211> LENGTH: 2843
<212> TYPE: PRT
<213> ORGANISM: Homo sapiens

<400> SEQUENCE: 1

Met Ala Ala Ala Ser Tyr Asp Gln Leu Leu Lys Gln Val Glu Ala Leu
1               5                   10                  15

Lys Met Glu Asn Ser Asn Leu Arg Gln Glu Leu Glu Asp Asn Ser Asn
            20                  25                  30

His Leu Thr Lys Leu Glu Thr Glu Ala Ser Asn Met Lys Glu Val Leu
        35                  40                  45

Lys Gln Leu Gln Gly Ser Ile Glu Asp Glu Ala Met Ala Ser Ser Gly
    50                  55                  60

Gln Ile Asp Leu Leu Glu Arg Leu Lys Glu Leu Asn Leu Asp Ser Ser
65                  70                  75                  80

Asn Phe Pro Gly Val Lys Leu Arg Ser Lys Met Ser Leu Arg Ser Tyr
                85                  90                  95

Gly Ser Arg Glu Gly Ser Val Ser Ser Arg Ser Gly Glu Cys Ser Pro
            100                 105                 110

Val Pro Met Gly Ser Phe Pro Arg Arg Gly Phe Val Asn Gly Ser Arg
        115                 120                 125

Glu Ser Thr Gly Tyr Leu Glu Glu Leu Glu Lys Glu Arg Ser Leu Leu
    130                 135                 140

Leu Ala Asp Leu Asp Lys Glu Glu Lys Glu Lys Asp Trp Tyr Tyr Ala
145                 150                 155                 160

Gln Leu Gln Asn Leu Thr Lys Arg Ile Asp Ser Leu Pro Leu Thr Glu
                165                 170                 175

Asn Phe Ser Leu Gln Thr Asp Met Thr Arg Arg Gln Leu Glu Tyr Glu
            180                 185                 190

Ala Arg Gln Ile Arg Val Ala Met Glu Glu Gln Leu Gly Thr Cys Gln
        195                 200                 205

Asp Met Glu Lys Arg Ala Gln Arg Arg Ile Ala Arg Ile Gln Gln Ile
    210                 215                 220

Glu Lys Asp Ile Leu Arg Ile Arg Gln Leu Leu Gln Ser Gln Ala Thr
225                 230                 235                 240

Glu Ala Glu Arg Ser Ser Gln Asn Lys His Glu Thr Gly Ser His Asp
                245                 250                 255

Ala Glu Arg Gln Asn Glu Gly Gln Gly Val Gly Glu Ile Asn Met Ala
            260                 265                 270

Thr Ser Gly Asn Gly Gln Gly Ser Thr Thr Arg Met Asp His Glu Thr
```

```
                275                 280                 285
Ala Ser Val Leu Ser Ser Ser Thr His Ser Ala Pro Arg Arg Leu
290                 295                 300

Thr Ser His Leu Gly Thr Lys Val Glu Met Val Tyr Ser Leu Leu Ser
305                 310                 315                 320

Met Leu Gly Thr His Asp Lys Asp Met Ser Arg Thr Leu Leu Ala
                325                 330                 335

Met Ser Ser Ser Gln Asp Ser Cys Ile Ser Met Arg Gln Ser Gly Cys
                340                 345                 350

Leu Pro Leu Leu Ile Gln Leu His Gly Asn Asp Lys Asp Ser Val
        355                 360                 365

Leu Leu Gly Asn Ser Arg Gly Ser Lys Glu Ala Arg Ala Arg Ala Ser
370                 375                 380

Ala Ala Leu His Asn Ile Ile His Ser Gln Pro Asp Asp Lys Arg Gly
385                 390                 395                 400

Arg Arg Glu Ile Arg Val Leu His Leu Leu Glu Gln Ile Arg Ala Tyr
                405                 410                 415

Cys Glu Thr Cys Trp Glu Trp Gln Glu Ala His Glu Pro Gly Met Asp
                420                 425                 430

Gln Asp Lys Asn Pro Met Pro Ala Pro Val Glu His Gln Ile Cys Pro
                435                 440                 445

Ala Val Cys Val Leu Met Lys Leu Ser Phe Asp Glu His Arg His
        450                 455                 460

Ala Met Asn Glu Leu Gly Gly Leu Gln Ala Ile Ala Glu Leu Leu Gln
465                 470                 475                 480

Val Asp Cys Glu Met Tyr Gly Leu Thr Asn Asp His Tyr Ser Ile Thr
                    485                 490                 495

Leu Arg Arg Tyr Ala Gly Met Ala Leu Thr Asn Leu Thr Phe Gly Asp
                500                 505                 510

Val Ala Asn Lys Ala Thr Leu Cys Ser Met Lys Gly Cys Met Arg Ala
        515                 520                 525

Leu Val Ala Gln Leu Lys Ser Glu Ser Glu Asp Leu Gln Gln Val Ile
        530                 535                 540

Ala Ser Val Leu Arg Asn Leu Ser Trp Arg Ala Asp Val Asn Ser Lys
545                 550                 555                 560

Lys Thr Leu Arg Glu Val Gly Ser Val Lys Ala Leu Met Glu Cys Ala
                565                 570                 575

Leu Glu Val Lys Lys Glu Ser Thr Leu Lys Ser Val Leu Ser Ala Leu
                580                 585                 590

Trp Asn Leu Ser Ala His Cys Thr Glu Asn Lys Ala Asp Ile Cys Ala
        595                 600                 605

Val Asp Gly Ala Leu Ala Phe Leu Val Gly Thr Leu Thr Tyr Arg Ser
610                 615                 620

Gln Thr Asn Thr Leu Ala Ile Ile Glu Ser Gly Gly Gly Ile Leu Arg
625                 630                 635                 640

Asn Val Ser Ser Leu Ile Ala Thr Asn Glu Asp His Arg Gln Ile Leu
                645                 650                 655

Arg Glu Asn Asn Cys Leu Gln Thr Leu Leu Gln His Leu Lys Ser His
                660                 665                 670

Ser Leu Thr Ile Val Ser Asn Ala Cys Gly Thr Leu Trp Asn Leu Ser
        675                 680                 685

Ala Arg Asn Pro Lys Asp Gln Glu Ala Leu Trp Asp Met Gly Ala Val
        690                 695                 700
```

-continued

```
Ser Met Leu Lys Asn Leu Ile His Ser Lys His Lys Met Ile Ala Met
705                 710                 715                 720

Gly Ser Ala Ala Ala Leu Arg Asn Leu Met Ala Asn Arg Pro Ala Lys
                725                 730                 735

Tyr Lys Asp Ala Asn Ile Met Ser Pro Gly Ser Ser Leu Pro Ser Leu
            740                 745                 750

His Val Arg Lys Gln Lys Ala Leu Glu Ala Glu Leu Asp Ala Gln His
        755                 760                 765

Leu Ser Glu Thr Phe Asp Asn Ile Asp Asn Leu Ser Pro Lys Ala Ser
770                 775                 780

His Arg Ser Lys Gln Arg His Lys Gln Ser Leu Tyr Gly Asp Tyr Val
785                 790                 795                 800

Phe Asp Thr Asn Arg His Asp Asp Asn Arg Ser Asp Asn Phe Asn Thr
                805                 810                 815

Gly Asn Met Thr Val Leu Ser Pro Tyr Leu Asn Thr Thr Val Leu Pro
            820                 825                 830

Ser Ser Ser Ser Ser Arg Gly Ser Leu Asp Ser Ser Arg Ser Glu Lys
        835                 840                 845

Asp Arg Ser Leu Glu Arg Glu Arg Gly Ile Gly Leu Gly Asn Tyr His
850                 855                 860

Pro Ala Thr Glu Asn Pro Gly Thr Ser Ser Lys Arg Gly Leu Gln Ile
865                 870                 875                 880

Ser Thr Thr Ala Ala Gln Ile Ala Lys Val Met Glu Glu Val Ser Ala
                885                 890                 895

Ile His Thr Ser Gln Glu Asp Arg Ser Ser Gly Ser Thr Thr Glu Leu
            900                 905                 910

His Cys Val Thr Asp Glu Arg Asn Ala Leu Arg Arg Ser Ser Ala Ala
        915                 920                 925

His Thr His Ser Asn Thr Tyr Asn Phe Thr Lys Ser Glu Asn Ser Asn
    930                 935                 940

Arg Thr Cys Ser Met Pro Tyr Ala Lys Leu Glu Tyr Lys Arg Ser Ser
945                 950                 955                 960

Asn Asp Ser Leu Asn Ser Val Ser Ser Asp Gly Tyr Gly Lys Arg
                965                 970                 975

Gly Gln Met Lys Pro Ser Ile Glu Ser Tyr Ser Glu Asp Asp Glu Ser
            980                 985                 990

Lys Phe Cys Ser Tyr Gly Gln Tyr Pro Ala Asp Leu Ala His Lys Ile
        995                 1000                1005

His Ser Ala Asn His Met Asp Asp Asn Asp Gly Glu Leu Asp Thr
    1010                1015                1020

Pro Ile Asn Tyr Ser Leu Lys Tyr Ser Asp Glu Gln Leu Asn Ser
    1025                1030                1035

Gly Arg Gln Ser Pro Ser Gln Asn Glu Arg Trp Ala Arg Pro Lys
    1040                1045                1050

His Ile Ile Glu Asp Glu Ile Lys Gln Ser Glu Gln Arg Gln Ser
    1055                1060                1065

Arg Asn Gln Ser Thr Thr Tyr Pro Val Tyr Thr Glu Ser Thr Asp
    1070                1075                1080

Asp Lys His Leu Lys Phe Gln Pro His Phe Gly Gln Gln Glu Cys
    1085                1090                1095

Val Ser Pro Tyr Arg Ser Arg Gly Ala Asn Gly Ser Glu Thr Asn
    1100                1105                1110
```

-continued

```
Arg Val Gly Ser Asn His Gly Ile Asn Gln Asn Val Ser Gln Ser
1115                1120                1125

Leu Cys Gln Glu Asp Asp Tyr Glu Asp Lys Pro Thr Asn Tyr
1130                1135                1140

Ser Glu Arg Tyr Ser Glu Glu Gln His Glu Glu Glu Arg
1145                1150                1155

Pro Thr Asn Tyr Ser Ile Lys Tyr Asn Glu Glu Lys Arg His Val
1160                1165                1170

Asp Gln Pro Ile Asp Tyr Ser Leu Lys Tyr Ala Thr Asp Ile Pro
1175                1180                1185

Ser Ser Gln Lys Gln Ser Phe Ser Phe Ser Lys Ser Ser Ser Gly
1190                1195                1200

Gln Ser Ser Lys Thr Glu His Met Ser Ser Ser Glu Asn Thr
1205                1210                1215

Ser Thr Pro Ser Ser Asn Ala Lys Arg Gln Asn Gln Leu His Pro
1220                1225                1230

Ser Ser Ala Gln Ser Arg Ser Gly Gln Pro Gln Lys Ala Ala Thr
1235                1240                1245

Cys Lys Val Ser Ser Ile Asn Gln Glu Thr Ile Gln Thr Tyr Cys
1250                1255                1260

Val Glu Asp Thr Pro Ile Cys Phe Ser Arg Cys Ser Ser Leu Ser
1265                1270                1275

Ser Leu Ser Ser Ala Glu Asp Glu Ile Gly Cys Asn Gln Thr Thr
1280                1285                1290

Gln Glu Ala Asp Ser Ala Asn Thr Leu Gln Ile Ala Glu Ile Lys
1295                1300                1305

Glu Lys Ile Gly Thr Arg Ser Ala Glu Asp Pro Val Ser Glu Val
1310                1315                1320

Pro Ala Val Ser Gln His Pro Arg Thr Lys Ser Ser Arg Leu Gln
1325                1330                1335

Gly Ser Ser Leu Ser Ser Glu Ser Ala Arg His Lys Ala Val Glu
1340                1345                1350

Phe Ser Ser Gly Ala Lys Ser Pro Ser Lys Ser Gly Ala Gln Thr
1355                1360                1365

Pro Lys Ser Pro Pro Glu His Tyr Val Gln Glu Thr Pro Leu Met
1370                1375                1380

Phe Ser Arg Cys Thr Ser Val Ser Ser Leu Asp Ser Phe Glu Ser
1385                1390                1395

Arg Ser Ile Ala Ser Ser Val Gln Ser Glu Pro Cys Ser Gly Met
1400                1405                1410

Val Ser Gly Ile Ile Ser Pro Ser Asp Leu Pro Asp Ser Pro Gly
1415                1420                1425

Gln Thr Met Pro Pro Ser Arg Ser Lys Thr Pro Pro Pro Pro
1430                1435                1440

Gln Thr Ala Gln Thr Lys Arg Glu Val Pro Lys Asn Lys Ala Pro
1445                1450                1455

Thr Ala Glu Lys Arg Glu Ser Gly Pro Lys Gln Ala Ala Val Asn
1460                1465                1470

Ala Ala Val Gln Arg Val Gln Val Leu Pro Asp Ala Asp Thr Leu
1475                1480                1485

Leu His Phe Ala Thr Glu Ser Thr Pro Asp Gly Phe Ser Cys Ser
1490                1495                1500

Ser Ser Leu Ser Ala Leu Ser Leu Asp Glu Pro Phe Ile Gln Lys
```

|       |       |       |       |       |       |       |       |       |       |
|-------|-------|-------|-------|-------|-------|-------|-------|-------|-------|
|       |       | 1505  |       |       |       | 1510  |       |       | 1515  |
| Asp   | Val   | Glu   | Leu   | Arg   | Ile   | Met   | Pro   | Pro   | Val   | Gln   | Glu   | Asn   | Asp   | Asn   |
|       |       | 1520  |       |       |       | 1525  |       |       | 1530  |
| Gly   | Asn   | Glu   | Thr   | Glu   | Ser   | Glu   | Gln   | Pro   | Lys   | Glu   | Ser   | Asn   | Glu   | Asn   |
|       |       | 1535  |       |       |       | 1540  |       |       | 1545  |
| Gln   | Glu   | Lys   | Glu   | Ala   | Glu   | Lys   | Thr   | Ile   | Asp   | Ser   | Glu   | Lys   | Asp   | Leu   |
|       |       | 1550  |       |       |       | 1555  |       |       | 1560  |
| Leu   | Asp   | Asp   | Ser   | Asp   | Asp   | Asp   | Asp   | Ile   | Glu   | Ile   | Leu   | Glu   | Glu   | Cys   |
|       |       | 1565  |       |       |       | 1570  |       |       | 1575  |
| Ile   | Ile   | Ser   | Ala   | Met   | Pro   | Thr   | Lys   | Ser   | Ser   | Arg   | Lys   | Ala   | Lys   | Lys   |
|       |       | 1580  |       |       |       | 1585  |       |       | 1590  |
| Pro   | Ala   | Gln   | Thr   | Ala   | Ser   | Lys   | Leu   | Pro   | Pro   | Val   | Ala   | Arg   | Lys   |
|       |       | 1595  |       |       |       | 1600  |       |       | 1605  |
| Pro   | Ser   | Gln   | Leu   | Pro   | Val   | Tyr   | Lys   | Leu   | Leu   | Pro   | Ser   | Gln   | Asn   | Arg   |
|       |       | 1610  |       |       |       | 1615  |       |       | 1620  |
| Leu   | Gln   | Pro   | Gln   | Lys   | His   | Val   | Ser   | Phe   | Thr   | Pro   | Gly   | Asp   | Asp   | Met   |
|       |       | 1625  |       |       |       | 1630  |       |       | 1635  |
| Pro   | Arg   | Val   | Tyr   | Cys   | Val   | Glu   | Gly   | Thr   | Pro   | Ile   | Asn   | Phe   | Ser   | Thr   |
|       |       | 1640  |       |       |       | 1645  |       |       | 1650  |
| Ala   | Thr   | Ser   | Leu   | Ser   | Asp   | Leu   | Thr   | Ile   | Glu   | Ser   | Pro   | Pro   | Asn   | Glu   |
|       |       | 1655  |       |       |       | 1660  |       |       | 1665  |
| Leu   | Ala   | Ala   | Gly   | Glu   | Gly   | Val   | Arg   | Gly   | Gly   | Ala   | Gln   | Ser   | Gly   | Glu   |
|       |       | 1670  |       |       |       | 1675  |       |       | 1680  |
| Phe   | Glu   | Lys   | Arg   | Asp   | Thr   | Ile   | Pro   | Thr   | Glu   | Gly   | Arg   | Ser   | Thr   | Asp   |
|       |       | 1685  |       |       |       | 1690  |       |       | 1695  |
| Glu   | Ala   | Gln   | Gly   | Gly   | Lys   | Thr   | Ser   | Ser   | Val   | Thr   | Ile   | Pro   | Glu   | Leu   |
|       |       | 1700  |       |       |       | 1705  |       |       | 1710  |
| Asp   | Asp   | Asn   | Lys   | Ala   | Glu   | Glu   | Gly   | Asp   | Ile   | Leu   | Ala   | Glu   | Cys   | Ile   |
|       |       | 1715  |       |       |       | 1720  |       |       | 1725  |
| Asn   | Ser   | Ala   | Met   | Pro   | Lys   | Gly   | Lys   | Ser   | His   | Lys   | Pro   | Phe   | Arg   | Val   |
|       |       | 1730  |       |       |       | 1735  |       |       | 1740  |
| Lys   | Lys   | Ile   | Met   | Asp   | Gln   | Val   | Gln   | Gln   | Ala   | Ser   | Ala   | Ser   | Ser   | Ser   |
|       |       | 1745  |       |       |       | 1750  |       |       | 1755  |
| Ala   | Pro   | Asn   | Lys   | Asn   | Gln   | Leu   | Asp   | Gly   | Lys   | Lys   | Lys   | Lys   | Pro   | Thr   |
|       |       | 1760  |       |       |       | 1765  |       |       | 1770  |
| Ser   | Pro   | Val   | Lys   | Pro   | Ile   | Pro   | Gln   | Asn   | Thr   | Glu   | Tyr   | Arg   | Thr   | Arg   |
|       |       | 1775  |       |       |       | 1780  |       |       | 1785  |
| Val   | Arg   | Lys   | Asn   | Ala   | Asp   | Ser   | Lys   | Asn   | Asn   | Leu   | Asn   | Ala   | Glu   | Arg   |
|       |       | 1790  |       |       |       | 1795  |       |       | 1800  |
| Val   | Phe   | Ser   | Asp   | Asn   | Lys   | Asp   | Ser   | Lys   | Lys   | Gln   | Asn   | Leu   | Lys   | Asn   |
|       |       | 1805  |       |       |       | 1810  |       |       | 1815  |
| Asn   | Ser   | Lys   | Val   | Phe   | Asn   | Asp   | Lys   | Leu   | Pro   | Asn   | Asn   | Glu   | Asp   | Arg   |
|       |       | 1820  |       |       |       | 1825  |       |       | 1830  |
| Val   | Arg   | Gly   | Ser   | Phe   | Ala   | Phe   | Asp   | Ser   | Pro   | His   | His   | Tyr   | Thr   | Pro   |
|       |       | 1835  |       |       |       | 1840  |       |       | 1845  |
| Ile   | Glu   | Gly   | Thr   | Pro   | Tyr   | Cys   | Phe   | Ser   | Arg   | Asn   | Asp   | Ser   | Leu   | Ser   |
|       |       | 1850  |       |       |       | 1855  |       |       | 1860  |
| Ser   | Leu   | Asp   | Phe   | Asp   | Asp   | Asp   | Asp   | Val   | Asp   | Leu   | Ser   | Arg   | Glu   | Lys   |
|       |       | 1865  |       |       |       | 1870  |       |       | 1875  |
| Ala   | Glu   | Leu   | Arg   | Lys   | Ala   | Lys   | Glu   | Asn   | Lys   | Glu   | Ser   | Glu   | Ala   | Lys   |
|       |       | 1880  |       |       |       | 1885  |       |       | 1890  |
| Val   | Thr   | Ser   | His   | Thr   | Glu   | Leu   | Thr   | Ser   | Asn   | Gln   | Gln   | Ser   | Ala   | Asn   |
|       |       | 1895  |       |       |       | 1900  |       |       | 1905  |

-continued

```
Lys Thr Gln Ala Ile Ala Lys Gln Pro Ile Asn Arg Gly Gln Pro
    1910            1915                1920

Lys Pro Ile Leu Gln Lys Gln Ser Thr Phe Pro Gln Ser Ser Lys
    1925            1930                1935

Asp Ile Pro Asp Arg Gly Ala Ala Thr Asp Glu Lys Leu Gln Asn
    1940            1945                1950

Phe Ala Ile Glu Asn Thr Pro Val Cys Phe Ser His Asn Ser Ser
    1955            1960                1965

Leu Ser Ser Leu Ser Asp Ile Asp Gln Glu Asn Asn Asn Lys Glu
    1970            1975                1980

Asn Glu Pro Ile Lys Glu Thr Glu Pro Pro Asp Ser Gln Gly Glu
    1985            1990                1995

Pro Ser Lys Pro Gln Ala Ser Gly Tyr Ala Pro Lys Ser Phe His
    2000            2005                2010

Val Glu Asp Thr Pro Val Cys Phe Ser Arg Asn Ser Ser Leu Ser
    2015            2020                2025

Ser Leu Ser Ile Asp Ser Glu Asp Asp Leu Leu Gln Glu Cys Ile
    2030            2035                2040

Ser Ser Ala Met Pro Lys Lys Lys Pro Ser Arg Leu Lys Gly
    2045            2050                2055

Asp Asn Glu Lys His Ser Pro Arg Asn Met Gly Gly Ile Leu Gly
    2060            2065                2070

Glu Asp Leu Thr Leu Asp Leu Lys Asp Ile Gln Arg Pro Asp Ser
    2075            2080                2085

Glu His Gly Leu Ser Pro Asp Ser Glu Asn Phe Asp Trp Lys Ala
    2090            2095                2100

Ile Gln Glu Gly Ala Asn Ser Ile Val Ser Ser Leu His Gln Ala
    2105            2110                2115

Ala Ala Ala Ala Cys Leu Ser Arg Gln Ala Ser Ser Asp Ser Asp
    2120            2125                2130

Ser Ile Leu Ser Leu Lys Ser Gly Ile Ser Leu Gly Ser Pro Phe
    2135            2140                2145

His Leu Thr Pro Asp Gln Glu Glu Lys Pro Phe Thr Ser Asn Lys
    2150            2155                2160

Gly Pro Arg Ile Leu Lys Pro Gly Glu Lys Ser Thr Leu Glu Thr
    2165            2170                2175

Lys Lys Ile Glu Ser Glu Ser Lys Gly Ile Lys Gly Gly Lys Lys
    2180            2185                2190

Val Tyr Lys Ser Leu Ile Thr Gly Lys Val Arg Ser Asn Ser Glu
    2195            2200                2205

Ile Ser Gly Gln Met Lys Gln Pro Leu Gln Ala Asn Met Pro Ser
    2210            2215                2220

Ile Ser Arg Gly Arg Thr Met Ile His Ile Pro Gly Val Arg Asn
    2225            2230                2235

Ser Ser Ser Ser Thr Ser Pro Val Ser Lys Lys Gly Pro Pro Leu
    2240            2245                2250

Lys Thr Pro Ala Ser Lys Ser Pro Ser Glu Gly Gln Thr Ala Thr
    2255            2260                2265

Thr Ser Pro Arg Gly Ala Lys Pro Ser Val Lys Ser Glu Leu Ser
    2270            2275                2280

Pro Val Ala Arg Gln Thr Ser Gln Ile Gly Gly Ser Ser Lys Ala
    2285            2290                2295
```

```
Pro Ser Arg Ser Gly Ser Arg Asp Ser Thr Pro Ser Arg Pro Ala
2300                2305                2310

Gln Gln Pro Leu Ser Arg Pro Ile Gln Ser Pro Gly Arg Asn Ser
    2315                2320                2325

Ile Ser Pro Gly Arg Asn Gly Ile Ser Pro Pro Asn Lys Leu Ser
2330                2335                2340

Gln Leu Pro Arg Thr Ser Ser Pro Ser Thr Ala Ser Thr Lys Ser
    2345                2350                2355

Ser Gly Ser Gly Lys Met Ser Tyr Thr Ser Pro Gly Arg Gln Met
2360                2365                2370

Ser Gln Gln Asn Leu Thr Lys Gln Thr Gly Leu Ser Lys Asn Ala
    2375                2380                2385

Ser Ser Ile Pro Arg Ser Glu Ser Ala Ser Lys Gly Leu Asn Gln
2390                2395                2400

Met Asn Asn Gly Asn Gly Ala Asn Lys Lys Val Glu Leu Ser Arg
    2405                2410                2415

Met Ser Ser Thr Lys Ser Ser Gly Ser Glu Ser Asp Arg Ser Glu
2420                2425                2430

Arg Pro Val Leu Val Arg Gln Ser Thr Phe Ile Lys Glu Ala Pro
    2435                2440                2445

Ser Pro Thr Leu Arg Arg Lys Leu Glu Glu Ser Ala Ser Phe Glu
2450                2455                2460

Ser Leu Ser Pro Ser Ser Arg Pro Ala Ser Pro Thr Arg Ser Gln
    2465                2470                2475

Ala Gln Thr Pro Val Leu Ser Pro Ser Leu Pro Asp Met Ser Leu
2480                2485                2490

Ser Thr His Ser Ser Val Gln Ala Gly Gly Trp Arg Lys Leu Pro
    2495                2500                2505

Pro Asn Leu Ser Pro Thr Ile Glu Tyr Asn Asp Gly Arg Pro Ala
2510                2515                2520

Lys Arg His Asp Ile Ala Arg Ser His Ser Glu Ser Pro Ser Arg
    2525                2530                2535

Leu Pro Ile Asn Arg Ser Gly Thr Trp Lys Arg Glu His Ser Lys
2540                2545                2550

His Ser Ser Ser Leu Pro Arg Val Ser Thr Trp Arg Arg Thr Gly
    2555                2560                2565

Ser Ser Ser Ser Ile Leu Ser Ala Ser Ser Glu Ser Ser Glu Lys
2570                2575                2580

Ala Lys Ser Glu Asp Glu Lys His Val Asn Ser Ile Ser Gly Thr
    2585                2590                2595

Lys Gln Ser Lys Glu Asn Gln Val Ser Ala Lys Gly Thr Trp Arg
2600                2605                2610

Lys Ile Lys Glu Asn Glu Phe Ser Pro Thr Asn Ser Thr Ser Gln
    2615                2620                2625

Thr Val Ser Ser Gly Ala Thr Asn Gly Ala Glu Ser Lys Thr Leu
2630                2635                2640

Ile Tyr Gln Met Ala Pro Ala Val Ser Lys Thr Glu Asp Val Trp
    2645                2650                2655

Val Arg Ile Glu Asp Cys Pro Ile Asn Asn Pro Arg Ser Gly Arg
2660                2665                2670

Ser Pro Thr Gly Asn Thr Pro Pro Val Ile Asp Ser Val Ser Glu
    2675                2680                2685

Lys Ala Asn Pro Asn Ile Lys Asp Ser Lys Asp Asn Gln Ala Lys
```

```
                2690                2695                2700

Gln Asn Val Gly Asn Gly Ser Val Pro Met Arg Thr Val Gly Leu
    2705                2710                2715

Glu Asn Arg Leu Asn Ser Phe Ile Gln Val Asp Ala Pro Asp Gln
    2720                2725                2730

Lys Gly Thr Glu Ile Lys Pro Gly Gln Asn Asn Pro Val Pro Val
    2735                2740                2745

Ser Glu Thr Asn Glu Ser Ser Ile Val Glu Arg Thr Pro Phe Ser
    2750                2755                2760

Ser Ser Ser Ser Ser Lys His Ser Ser Pro Ser Gly Thr Val Ala
    2765                2770                2775

Ala Arg Val Thr Pro Phe Asn Tyr Asn Pro Ser Pro Arg Lys Ser
    2780                2785                2790

Ser Ala Asp Ser Thr Ser Ala Arg Pro Ser Gln Ile Pro Thr Pro
    2795                2800                2805

Val Asn Asn Asn Thr Lys Lys Arg Asp Ser Lys Thr Asp Ser Thr
    2810                2815                2820

Glu Ser Ser Gly Thr Gln Ser Pro Lys Arg His Ser Gly Ser Tyr
    2825                2830                2835

Leu Val Thr Ser Val
    2840

<210> SEQ ID NO 2
<211> LENGTH: 335
<212> TYPE: PRT
<213> ORGANISM: Homo sapiens

<400> SEQUENCE: 2

Met Ser Lys Arg Lys Ala Pro Gln Glu Thr Leu Asn Gly Gly Ile Thr
1               5                   10                  15

Asp Met Leu Thr Glu Leu Ala Asn Phe Glu Lys Asn Val Ser Gln Ala
                20                  25                  30

Ile His Lys Tyr Asn Ala Tyr Arg Lys Ala Ala Ser Val Ile Ala Lys
            35                  40                  45

Tyr Pro His Lys Ile Lys Ser Gly Ala Glu Ala Lys Lys Leu Pro Gly
        50                  55                  60

Val Gly Thr Lys Ile Ala Glu Lys Ile Asp Glu Phe Leu Ala Thr Gly
65                  70                  75                  80

Lys Leu Arg Lys Leu Glu Lys Ile Arg Gln Asp Asp Thr Ser Ser Ser
                85                  90                  95

Ile Asn Phe Leu Thr Arg Val Ser Gly Ile Gly Pro Ser Ala Ala Arg
            100                 105                 110

Lys Phe Val Asp Glu Gly Ile Lys Thr Leu Glu Asp Leu Arg Lys Asn
        115                 120                 125

Glu Asp Lys Leu Asn His His Gln Arg Ile Gly Leu Lys Tyr Phe Gly
    130                 135                 140

Asp Phe Glu Lys Arg Ile Pro Arg Glu Glu Met Leu Gln Met Gln Asp
145                 150                 155                 160

Ile Val Leu Asn Glu Val Lys Lys Val Asp Ser Glu Tyr Ile Ala Thr
                165                 170                 175

Val Cys Gly Ser Phe Arg Arg Gly Ala Glu Ser Ser Gly Asp Met Asp
            180                 185                 190

Val Leu Leu Thr His Pro Ser Phe Thr Ser Glu Ser Thr Lys Gln Pro
        195                 200                 205
```

-continued

```
Lys Leu Leu His Gln Val Val Glu Gln Leu Gln Lys Val His Phe Ile
    210             215                 220
Thr Asp Thr Leu Ser Lys Gly Glu Thr Lys Phe Met Gly Val Cys Gln
225             230                 235                 240
Leu Pro Ser Lys Asn Asp Glu Lys Glu Tyr Pro His Arg Arg Ile Asp
            245                 250                 255
Ile Arg Leu Ile Pro Lys Asp Gln Tyr Tyr Cys Gly Val Leu Tyr Phe
            260                 265                 270
Thr Gly Ser Asp Ile Phe Asn Lys Asn Met Arg Ala His Ala Leu Glu
            275                 280                 285
Lys Gly Phe Thr Ile Asn Glu Tyr Thr Ile Arg Pro Leu Gly Val Thr
    290                 295                 300
Gly Val Ala Gly Glu Pro Leu Pro Val Asp Ser Glu Lys Asp Ile Phe
305             310                 315                 320
Asp Tyr Ile Gln Trp Lys Tyr Arg Glu Pro Lys Asp Arg Ser Glu
                325                 330                 335
```